(12) United States Patent
Sims et al.

(10) Patent No.: US 10,576,202 B2
(45) Date of Patent: Mar. 3, 2020

(54) FLOW RATE MEASUREMENT AND CONTROL OF INFUSION DEVICES

(71) Applicant: The General Hospital Corporation, Boston, MA (US)

(72) Inventors: Nathaniel M. Sims, Milton, MA (US); Eric John Flachbart, Newport Center, VT (US); Duane Edward Allen, Sheffield, VT (US); Benjamin James Chomyn, Fairfield, VT (US); Paul C. Henninge, Burlington, VT (US); Joseph Matthew Pasquence, Plainfield, VT (US); Andrew W. Asack, Barton, VT (US); Michael H. Wollowitz, Chatham, NY (US); Rolf E. Zuk, Monroe, NH (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/526,193

(22) PCT Filed: Nov. 12, 2015

(86) PCT No.: PCT/US2015/060304
§ 371 (c)(1),
(2) Date: May 11, 2017

(87) PCT Pub. No.: WO2016/077534
PCT Pub. Date: May 19, 2016

(65) Prior Publication Data
US 2018/0177945 A1 Jun. 28, 2018

Related U.S. Application Data

(60) Provisional application No. 62/078,930, filed on Nov. 12, 2014.

(51) Int. Cl.
*A61M 5/168* (2006.01)
*G01G 17/06* (2006.01)
(Continued)

(52) U.S. Cl.
CPC .......... *A61M 5/16877* (2013.01); *A61M 5/14* (2013.01); *A61M 5/1689* (2013.01);
(Continued)

(58) Field of Classification Search
CPC ................ A61M 5/16877; A61M 5/14; A61M 5/16813; A61M 5/16827; A61M 5/1689;
(Continued)

(56) References Cited

U.S. PATENT DOCUMENTS 3,563,090 A * 2/1971 Deltour ............... A61M 5/1689
128/DIG. 13
3,601,124 A 8/1971 Peret et al.
(Continued)

OTHER PUBLICATIONS

International Search Report and Written Opinion dated Mar. 4, 2016 in international application No. PCT/US2015/060304, 37 pgs.
(Continued)

*Primary Examiner* — Brandy S Lee
*Assistant Examiner* — Hong-Van N Trinh
(74) *Attorney, Agent, or Firm* — Fish & Richardson P.C.

(57) ABSTRACT

An infusion apparatus includes a housing and a chamber configured to be connected to the housing. The apparatus further includes a weight sensor coupled to a load connector connected to the housing and an optical sensor disposed in the housing. The weight sensor is configured to generate a first signal based on a measured weight of the fluid container attached to the housing in a weight-bearing configuration. The optical sensor is configured to generate a second signal based on detecting drops of the fluid traversing the chamber. The apparatus also includes a flow control mechanism to
(Continued)

control a flow rate of the fluid into an outlet channel. The apparatus includes one or more processing devices configured to perform operations including transmitting a control signal to the flow control mechanism to adjust the flow rate.

15 Claims, 23 Drawing Sheets

(51) Int. Cl.
*A61M 5/14* (2006.01)
*G01F 1/66* (2006.01)
*G01F 1/72* (2006.01)
*G01N 15/14* (2006.01)
*G01G 19/18* (2006.01)
*A61M 5/172* (2006.01)

(52) U.S. Cl.
CPC .... *A61M 5/16813* (2013.01); *A61M 5/16827* (2013.01); *A61M 5/16895* (2013.01); *G01F 1/661* (2013.01); *G01F 1/72* (2013.01); *G01G 17/06* (2013.01); *G01N 15/1429* (2013.01); *A61M 5/172* (2013.01); *A61M 2205/121* (2013.01); *A61M 2205/3306* (2013.01); *A61M 2205/3313* (2013.01); *A61M 2205/3365* (2013.01); *A61M 2205/3584* (2013.01); *A61M 2205/505* (2013.01); *A61M 2205/52* (2013.01); *G01G 19/18* (2013.01); *G01N 2015/1493* (2013.01)

(58) Field of Classification Search
CPC ........ A61M 5/16895; A61M 2205/121; A61M 2205/3306; A61M 2205/3313; A61M 5/16881; A61M 5/16886; A61M 5/172; A61M 5/1411; A61M 5/16804; A61M 5/168814; A61M 2005/1401; A61M 5/1684; A61M 5/16845; A61M 5/168; A61M 2205/52; G01F 1/661; G01F 1/72; G01G 19/18; G01G 17/04; G01G 17/06; G01G 19/14; G01G 19/16; F01F 1/72
See application file for complete search history.

(56) References Cited

U.S. PATENT DOCUMENTS

| | | | |
|---|---|---|---|
| 3,999,542 A * | 12/1976 | Shaw | A61M 5/16845 604/507 |
| 4,137,915 A | 2/1979 | Kamen | |
| 4,411,649 A * | 10/1983 | Kamen | A61M 5/16895 128/DIG. 13 |
| 4,634,426 A | 1/1987 | Kamen | |
| 4,670,007 A | 6/1987 | Wheeldon et al. | |
| 4,747,828 A | 5/1988 | Tseo | |
| 4,718,896 A | 12/1988 | Arndt et al. | |
| 4,889,528 A * | 12/1989 | Nadai | A61M 5/16895 604/65 |
| 5,078,683 A | 1/1992 | Sancoff et al. | |
| 6,202,711 B1 | 3/2001 | Martucci et al. | |
| 6,269,340 B1 * | 7/2001 | Ford | A61M 5/172 705/3 |
| 7,543,516 B2 | 6/2009 | Siefert | |
| 7,763,877 B2 | 7/2010 | Paz | |
| 8,328,763 B2 | 12/2012 | Traversaz | |
| 8,471,231 B2 | 6/2013 | Paz | |
| 8,579,859 B2 | 11/2013 | Kramer et al. | |
| 8,622,979 B2 | 1/2014 | Hungerford et al. | |
| 2003/0048185 A1 * | 3/2003 | Citrenbaum | A61M 5/16895 340/540 |
| 2004/0059295 A1 | 3/2004 | Cartledge et al. | |
| 2004/0087895 A1 | 5/2004 | Cho et al. | |
| 2005/0096593 A1 * | 5/2005 | Pope | A61M 5/1452 604/122 |
| 2006/0079862 A1 | 4/2006 | Genosar | |
| 2006/0144155 A1 | 7/2006 | Liu | |
| 2009/0264857 A1 * | 10/2009 | Susi | F04B 43/082 604/506 |
| 2011/0046533 A1 | 2/2011 | Stefani et al. | |
| 2012/0283630 A1 * | 11/2012 | Lee | A61M 5/16827 604/65 |
| 2013/0092288 A1 | 4/2013 | Schriber | |
| 2014/0243738 A1 | 8/2014 | Kramer et al. | |
| 2014/0283620 A1 | 9/2014 | Kolko et al. | |
| 2014/0318639 A1 * | 10/2014 | Peret | F16K 31/02 137/386 |

OTHER PUBLICATIONS

International Preliminary Report on Patentability in International Application No. PCT/US2015/060304, dated May 16, 2017, 20 pages.

Drip Eye NE-1 Automatic Infusion Control Equipment, Parama-Tech, Oct. 1, 2006, 2 pages.

Supplementary European Search Report issued in EP 15858209 dated Jul. 9, 2018 (10 pages).

* cited by examiner

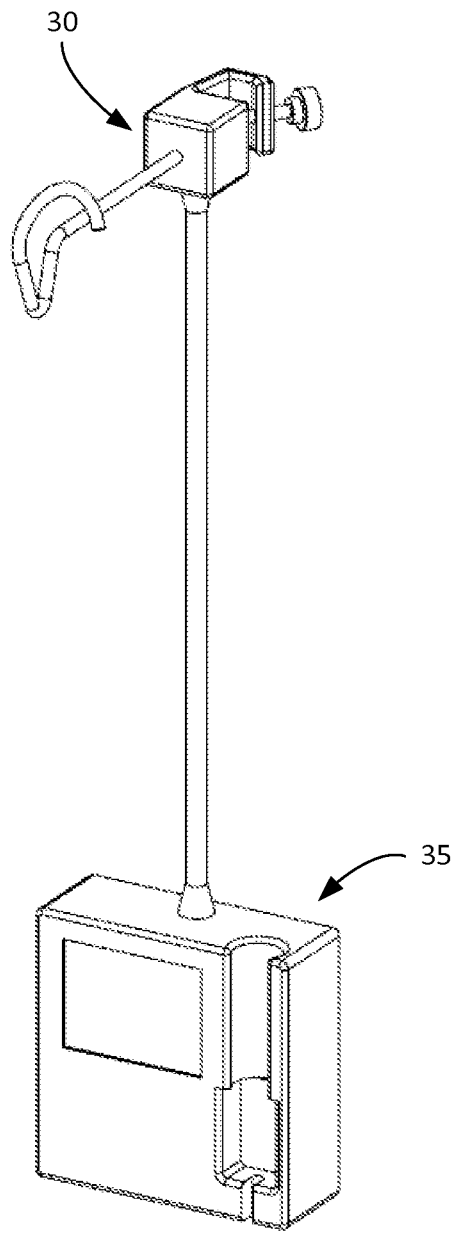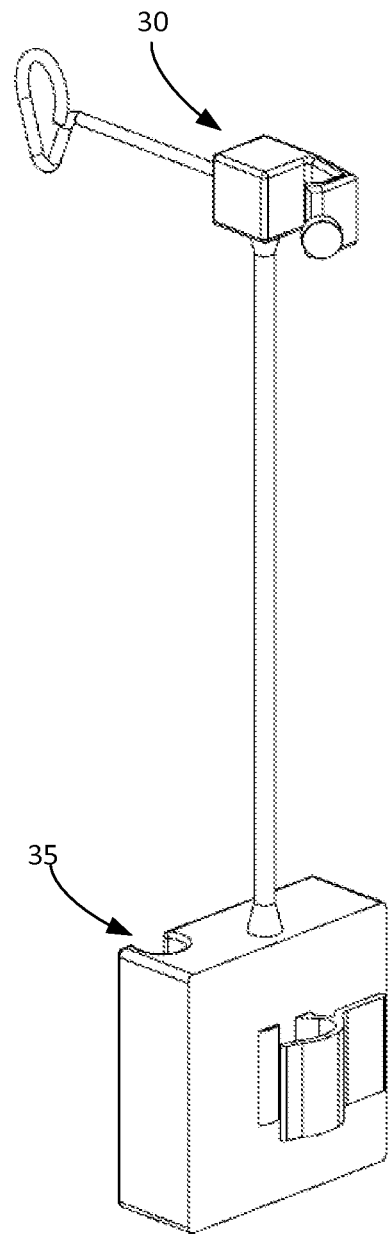
FIG. 12C  FIG. 12D

FLOW RATE MEASUREMENT AND CONTROL OF INFUSION DEVICES

CROSS-REFERENCE TO RELATED APPLICATION

This application is a U.S. National Phase Application under 35 U.S.C. § 371 of International Patent Application No. PCT/US2015/060304, filed on Nov. 12, 2015, which claims priority to U.S. Provisional Application No. 62/078,930 filed on Nov. 12, 2014, the entire content of which is incorporated herein by reference.

TECHNICAL FIELD

The technology described in this document relates to infusion pumps.

BACKGROUND

Infusion pumps are used for infusing fluids, which can include drugs or nutrients, into circulatory systems of humans or animals. Infusion pumps can be of various types, such as syringe infusion pumps and volumetric infusion pumps. Volumetric infusion pumps function by dispensing fluid from an intravenous (IV) fluid bag (also referred in as an IV bag or IV container) suspended at a head height relative to the patient. Mechanisms for regulating fluid flow from an IV bag can include, for example, rotary and linear peristaltic mechanisms as well as piston driven cartridge mechanisms. Such mechanisms can include a motor to drive the pumping element in an active fashion to provide a fluid flow from the bag. In the case of a rotary peristaltic mechanism, a motor can be used to cause a wheel with protrusions to rotate in contact with the tubing, causing fluid to be pushed through the tube. In the case of a linear peristaltic mechanism, a motor can be used to turn a crankshaft or camshaft which pushes fingers into the tubing in a peristaltic wave, thereby causing the fluid flow. In the case of a piston cartridge mechanism, a motor can be used to cycle the piston back and forth and in conjunction with two or more check valves to cause fluid flow.

In the case of peristaltic pumps, the fluid tubing is located with respect to the pumping elements such that sufficient closure of the tubing is provided to ensure pumping action when fluid flow is desired and full closure of the tubing when the pump is stopped. To allow a user to install a new tubing set for each new therapy, a door is typically used to function both as a platen which supports the tubing as the fingers pump against it, as well as to ensure that the tubing remains in communication with the pumping fingers such that the tube is always compressed at one or more points. In the event that the door does not close properly or the tubing is not fully closed by one or more of the fingers, free flow of fluid due to gravity can occur resulting in an overdose of medication to the patient. In addition, the fluid flow rate can be computed based on the speed of the motor. The motor is set to a particular RPM, which by the nature of the cross sectional area of the tubing and the gearing of the mechanism corresponds to an expected fluid flow. Since the pump measures only motor RPM and not actual fluid flow, errors can be caused if the tubing cross sectional area is less than what is expected due to, for example, non-elastic deformation of the tubing. Also, the precise location of the tubing set in relation to the mechanism requires precision bearings and other mechanical features, which can add cost and complexity and can detract from the reliability of the pumps.

In addition, such positive pressure pumps pose the hazard of pumping air into the patient, potentially causing air embolism. Even though sensors can be added to detect the presence of air in the tube set, the sensors are subject to false alarms as well as reliability issues. Typical medical fluid infusion pumps also can be subject to difficulties in accurately sensing the exhaustion of fluid from the IV bag, or upstream or downstream occlusion.

SUMMARY

The present disclosure is related to an infusion apparatus that dispenses medical fluid contained in an intravenous (IV) fluid-container to a patient through an outlet channel such as a tube. The infusion apparatus can dispense the fluid using a flow control mechanism, which can include, for example, a gravity-driven flow control mechanism, a volumetric pump, or other appropriate device to control a fluid flow. The infusion apparatus controls flow of the medical fluid using multiple sensing mechanisms. The multiple sensing mechanisms can use characteristics of the flow to determine the flow rate of medical fluid into the patient. The infusion apparatus further includes a cartridge with a drip chamber. The drip chamber and the infusion apparatus cooperate to form a drop detector that can count the number of drops of medical fluid over a period of time. In addition, the infusion apparatus can also include a weight sensor that determines changes in weight of the IV container. One or more processors in the infusion apparatus can be configured to compute the expected drop size based on, for example, density and viscosity information obtained from an electronic library or repository of information on medical fluids. The one or more processors can be configured to execute a process to estimate a flow rate based on the counted number of drops. The one or more processors can also be configured to execute a process for estimating a flow rate based on the weight measurements. The one or more processors can also be configured to estimate a flow rate based on, for example, a duty cycle, a load, a duration of operation, or other characteristics of the flow control mechanism. By relying on two or more estimates of the flow rate, the technology described in this document may allow for controlling the flow rate of an infusion device with a high degree of accuracy.

In one aspect, this document describes an infusion apparatus that dispenses fluid from a fluid-container into an outlet channel. The apparatus includes a housing, and a load connector attached to the housing and configured to accept a fluid container to be attached to the housing in a weight-bearing configuration. The apparatus also includes a chamber configured to be connected to the housing such that the chamber is disposed in a fluid path between the fluid container and the outlet channel. The chamber is configured to enable formation of drops as the fluid traverses the chamber. The apparatus further includes a weight sensor and an optical sensor. The weight sensor is coupled to the load connector, and is configured to generate a first signal based on a measured weight of the fluid-container attached to the housing in the weight-bearing configuration. The optical sensor is disposed in the housing and configured to generate a second signal based on measuring a flow rate as a function of a number of drops of fluid traversing the chamber. The apparatus also includes a flow control mechanism disposed in the fluid path between the fluid container and the outlet channel. The flow control mechanism is configured to control a flow of fluid into the outlet channel based on the first signal from the weight sensor and on the second signal from the optical sensor.

In a further aspect, this document describes an infusion apparatus that dispenses fluid from a fluid container into an outlet channel. The apparatus includes a housing and a load connector attached to the housing and configured to accept the fluid container to be attached to the housing in a weight-bearing configuration. The apparatus includes a chamber configured to be connected to the housing such that the chamber is disposed in a fluid path between the fluid container and the outlet channel. The chamber is configured to enable formation of drops as the fluid traverses the chamber. The apparatus includes a weight sensor coupled to the load connector. The weight sensor is configured to generate a weight signal based on a measured weight of the fluid container attached to the housing in the weight-bearing configuration. The apparatus includes an optical sensor disposed in the housing and configured to generate drop signals based on detecting the drops of the fluid traversing the chamber. The apparatus includes a flow control mechanism disposed in the fluid path between the fluid container and the outlet channel. The flow control mechanism is configured to control a flow rate of the fluid in the outlet channel. The apparatus includes one or more processing devices configured to execute machine-readable instructions to perform operations. The operations include accessing a representation of a medical fluid library that includes information on fluid parameters for a plurality of medical fluids, and computing a first estimate of a flow rate of the fluid based on the drop signals and the fluid parameters of a selected medical fluid of the plurality of medical fluids. The operations further include computing a second estimate of the flow rate of the fluid based on the weight signal, and transmitting a control signal to the flow control mechanism to adjust the flow rate of the fluid responsive to determining that a difference between the first estimate and the second estimate exceeds a threshold condition.

In another aspect, this document describes an infusion apparatus for dispensing a fluid to an outlet channel. The apparatus includes a weight sensor module configured to generate a first signal based on measuring a weight of a fluid-container dispensing the fluid, and a flow sensor module configured to generate a second signal based on measuring a flow rate as a function of a number of drops of fluid formed in traversing a drop forming section of a fluid path connecting the fluid-container and the outlet channel. The apparatus further includes a flow control mechanism disposed in the fluid path between the fluid container and the outlet channel. The flow control mechanism is configured to control a flow of fluid into the outlet channel based on the first signal and the second signal.

In a further aspect, this document describes an infusion apparatus for dispensing a fluid to an outlet channel. The apparatus includes a weight sensor module configured to generate a weight signal based on measuring a weight of a fluid container dispensing the fluid. The apparatus includes a flow sensor module configured to generate drop signals based on detecting drops of fluid formed in and traversing a fluid path connecting the fluid container and the outlet channel. The apparatus includes a flow control mechanism disposed in the fluid path between the fluid container and the outlet channel. The flow control mechanism is configured to control a flow rate of the fluid in the outlet channel. The apparatus includes one or more processing devices configured to execute machine-readable instructions to perform operations. The operations include accessing a representation of a medical fluid library that includes information on fluid parameters for a plurality of medical fluids, and computing a first estimate of a flow rate of the fluid based on the drop signals and the fluid parameters of a selected medical fluid of the plurality of medical fluids. The operations further include computing a second estimate of the flow rate of the fluid based on the weight signal, and transmitting a control signal to the flow control mechanism to adjust the flow rate of the fluid responsive to determining that a difference between the first estimate and the second estimate exceeds a threshold condition.

In another aspect, this document describes a method of dispensing fluid from a fluid container into an outlet channel. The method includes receiving, from a weight sensor, a weight signal based on a measured weight of the fluid-container attached to a housing of an infusion device in a weight-bearing configuration, and receiving, from a drop counting sensor, a flow-rate signal based on measuring a flow rate as a function of a number of drops of fluid traversing a drip chamber. The method also includes controlling, using a flow control mechanism, a flow of fluid into the outlet channel based on the weight signal from the weight sensor and on the flow-rate signal from the drop counting sensor.

In another aspect, this document describes a method of fault-management in an infusion device. The method includes determining whether a fault condition has occurred in an infusion device that is configured to accept a cartridge including a drip chamber; and activating an ejection mechanism to eject the cartridge upon determining an occurrence of the fault condition.

Implementations can include one or more of the following features. In some examples, the housing can include a receptacle for accepting an external cartridge that includes the chamber. The optical sensor can include a light emitting diode and an optical detector. The apparatus can include one or more processing devices configured to measure the flow rate from a measured number of drops based on an expected value of a volume per drop. The one or more processing devices can be further configured to determine a weight of the fluid container based on the weight signal from the weight sensor. The weight sensor can include a load cell. The load cell can include a beam attached to the load connector and a strain gauge attached to the beam. The load cell can include a tank circuit in which an oscillation frequency varies as a function of the fluid-container. The optical sensor can include an imaging device.

In some examples, the flow control mechanism can include an electronically controllable clamp or valve. The electronically controllable clamp or valve can be controlled using a control signal generated by one or more processing devices based on the weight signal of the weight sensor and drop number signal from the optical sensor. The flow control mechanism can include an adjustable tubing restrictor. The flow control mechanism can include a volumetric pump configured to provide a substantially fixed volume of fluid per pumping cycle. The volumetric pump can be a positive displacement pump. The flow control mechanism can be further configured to control the flow of fluid into the outlet channel based on a pump speed of the volumetric pump. The positive displacement pump can be a linear peristaltic pump. The weight sensor can be disposed at a lower vertical level with respect to the optical sensor and the flow control mechanism. The weight sensor can be disposed in the housing at a higher vertical level with respect to the optical sensor and the flow control mechanism.

In some examples, the drop forming section of the fluid path can include a hollow chamber. The apparatus can include a receptacle for receiving a cartridge that includes the drop forming section of the fluid path. The weight sensor module can be disposed within a housing of the apparatus. The apparatus can include a load connector configured to connect the fluid-container to the weight sensor such that the weight of the fluid-container can be measured by the weight sensor. The flow sensor module can include an optical sensor configured to measure the number of drops traversing the drop forming section.

In some examples, the infusion pump can be a gravity-driven infusion pump. The drop counting sensor can include an optical sensor. The flow control mechanism can be controlled using a control signal generated based on the weight signal from the weight sensor and on the flow-rate signal from the drop counting sensor. The flow control mechanism can include a linear peristaltic pump. The flow control mechanism can include a rotary peristaltic pump.

In some examples, the representation of the medical fluid library that includes the information on the fluid parameters for the plurality of medical fluids can be stored on one or more storage devices. The machine-readable instructions can be stored on the one or more storage devices. The one or more storage devices can be connected to the one or more processing devices. The apparatus can include one or more storage devices storing the representation of the medical fluid library that can include the information on the fluid parameters for the plurality of medical fluids, and and the machine-readable instructions.

In some examples, activating the ejection mechanism can include applying a force on a latch arm engaged with the cartridge to move the latch arm from a closed position through an intermediate position to an open position. The ejection mechanism can be configured such that, when the latch arm is between the closed position and the intermediate position, the latch arm is biased towards the closed position, and, when the latch arm is between the intermediate position and the open position, the latch arm is biased towards the open position. Applying the force on the latch arm can include applying the force by activating a motor. A first estimate of a flow rate through the infusion device can be computed based on a number of drops of fluid traversing the drip chamber and whether a fault condition has occurred can be determined based on the first estimate of the flow rate. A second estimate of a flow rate through the infusion device can be computed based on a weight of an IV container connected to the infusion device and whether the fault condition has occurred can be determined based on the first estimate and second estimate of the flow rate. In some implementations, a third estimate of the flow rate through the infusion device can be computed based on a pump speed of a volumetric pump of the infuser, and whether the fault condition has occurred can be determined based on the first, second, and third estimates of the flow rate.

In some examples, computing the first estimate can include computing an expected drop sized based on the fluid parameters of the selected medical fluid. The fluid parameters of the selected medical fluid can include at least one of a specific gravity, viscosity, and opacity of the selected medical fluid.

In some examples, transmitting the control signal to the flow control mechanism can include computing the difference between the first estimate and the second estimate and comparing the difference to the threshold condition. The drop signals can be indicative of a number of drops in a first time period and a number of drops in at least a second time period. Computing the first estimate can include computing the first estimate of the flow rate based on an average number of drops in the first time period and the second time period. Computing the first estimate of the flow rate can include comparing the number of drops detected in the first time period with the number of drops detected in the second time period, and computing the first estimate of the flow rate based on the average number of drops based on one of the first time period and the second time period.

In some examples, the weight signal can be indicative of the measured weight in a first time period and the measured weight in at least a second time period. Computing the second estimate can further include computing the second estimate of the flow rate based on an average measured weight in the first time period and the second time period. Computing the second estimate can further include comparing the measured weight in the first time period with the measured weight in the second time period. Computing the second estimate can further computing the second estimate of the flow rate based on the measured weight of one of the first time period and the second time period.

In some examples, the operations can further include computing a third estimate of the flow rate through the infusion apparatus based on a pump speed of a volumetric pump of the infusion apparatus. The operations can further include transmitting the control signal to the flow control mechanism to adjust the flow rate of the fluid based on the first estimate, the second estimate, and the third estimate.

In some examples, the operations can further include, before computing the first estimate, receiving from a user interface a selection indicative of the selected medical fluid.

In various implementations, the technologies described in this disclosure provide one or more of the following advantages. The weight sensor of the infusion apparatus can be operated in a deflection range in between that of load cells and spring balance scales. The weight sensor includes a spring that is stiff enough such that the time response is sufficiently fast and mechanical oscillation are sufficiently minimized. Deflections in the spring are small and the spring is protected from overloads, so loss of calibration due to excess strain is reduced or inhibited. Because the full spring deflection is measured, rather than just the strain over small regions, the spring can be smaller and simpler than a typical load cell. The difficulties of fabricating and securely attaching strain gauges is eliminated by the designs described herein, and the output signal is more robust and more easily measured. Compared to a spring balance the displacement is small, so springs smaller than those found in spring balances can be used, thus reducing the overall device size by comparison.

The use of two sensors to determine the flow rate of the delivered medical fluid enables increased accuracy and resolution. Any discrepancy in the flow rates determined using the different sensors provides a fail-safe mechanism to prevent incorrect dosing of drugs to patients. The two sensors also cooperate to determine whether the flow rate needs to be adjusted, providing an accurate and precise way of delivering a desired amount of drug to a patient.

The infusion devices described in this disclosure further include elements that can be produced rapidly and inexpensively using common materials, such as common polymers. Affordable standard electromechanical components can be implemented without sacrifice to the accuracy or precision of the infusion apparatus. As a result, these devices can be fabricated at a low total cost while maintaining required performance attributes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 12C is a front perspective view of a further example of an infuser.

FIG. 12D is a rear perspective view of the infuser of FIG. 12C.

Like reference symbols in the various drawings indicate like elements.

DETAILED DESCRIPTION

This disclosure describes medical intravenous infusion devices for use in fluid delivery from fluid-containers (also referred to as "IV containers"). The fluid delivery can occur through both deterministic and non-deterministic flow control mechanisms. In some implementations, the infusion devices (also referred to herein simply as "infusers") include a gravity-driven system that is controlled without the use of pumps. In some implementations, the infusion devices include a volumetric pump and/or positive displacement pump. The volumetric pump can be, for example, a rotary peristaltic pump or a linear peristaltic pump.

In some implementations, the flow control mechanism can be controlled with a high degree of accuracy. A user may input into a central processor (e.g., one or more processors) one or more parameters representing information about a medical fluid to be delivered. Based on the inputted information about the medical fluid, the infuser can execute a control process that determines the flow rate of the infuser. The infuser can further determine the amount of medical fluid delivered based on measuring the weight of a connected IV container and/or by measuring the number of drops of fluid detected. By determining the amount of fluid delivered in multiple ways, the infusion devices described herein can provide a safe and accurate way of regulating delivery of the fluid to a patient.

Figure 1A:
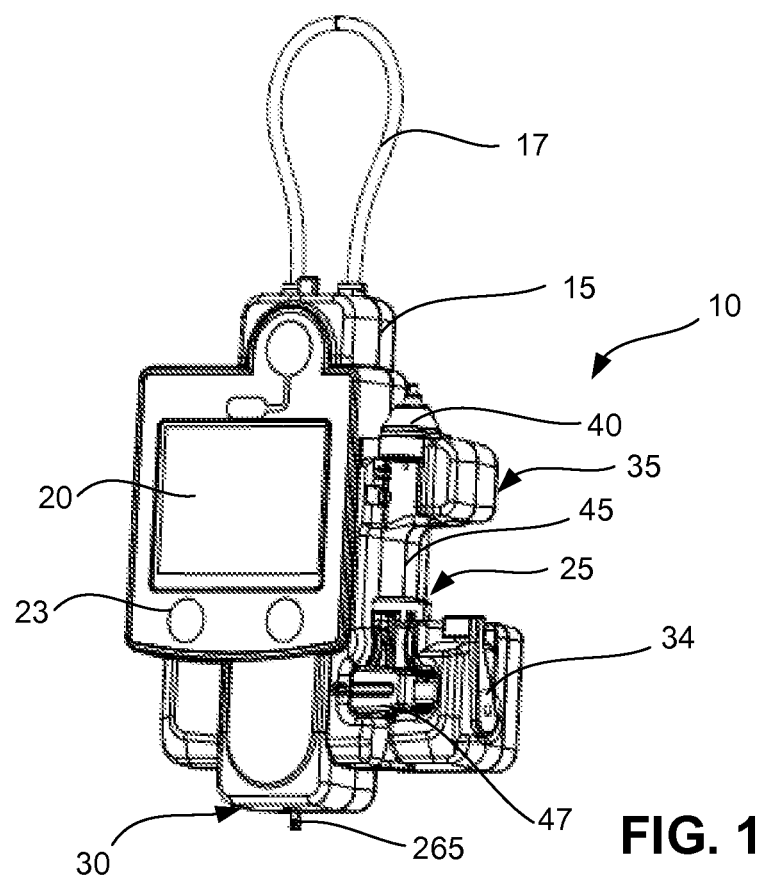
FIGS. 1A and 1B are the front and rear perspective views, respectively, of an example of an infuser.
Figure 1B:
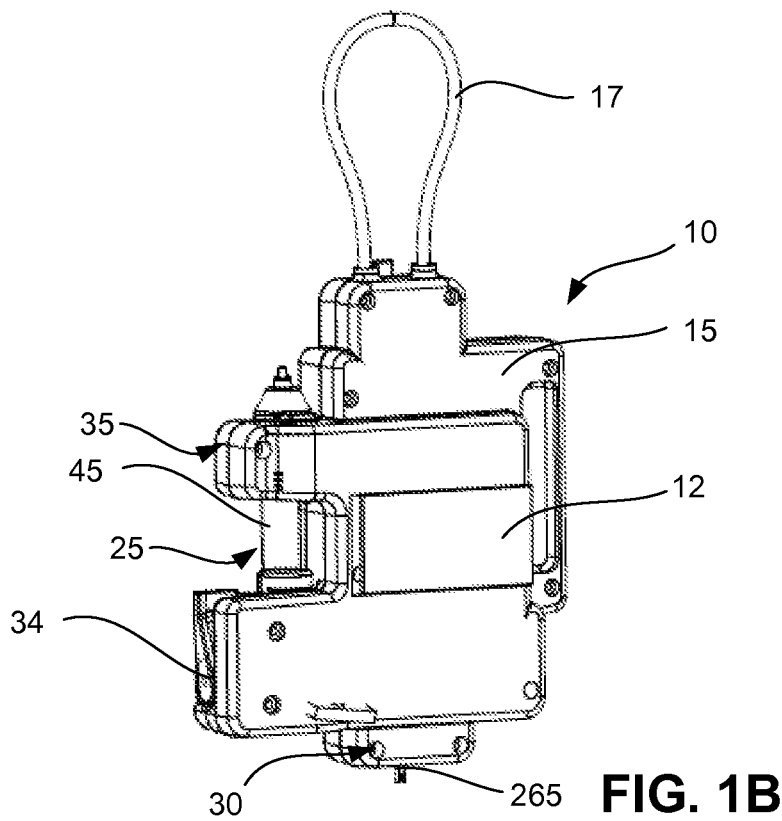

FIGS. 1A and 1B, respectively, show front and rear perspective views of an example of an infuser or infusion system 10, which includes a chassis 15, a display 20, a cartridge 25, and a weight sensor 30. The chassis 15 houses electrical and mechanical components for functionality of the infuser. In some implementations, the chassis 15 includes a receptacle for accepting the cartridge 25.

Referring to FIG. 1B, the rear of the infuser 10 includes a housing for a power source 12. The top of chassis 15 includes a loop 17 for hanging the infuser 10 on an IV pole or other support device. The display 20 allows a user to view information pertaining to treatment and to input additional information and instructions to the infuser. For example, the display 20 can be a color touchscreen display. Additional control buttons 23 can be disposed on the chassis.

The infuser includes at least two independent detectors for monitoring the flow rate: an automated drop detector 35 and the weight sensor 30 that continuously measures the weight of an IV container (not shown). The drop detector 35 detects drops that fall through a drip chamber 45 of the cartridge 25. The weight sensor 30 measures the weight of an IV container that has been hung on a load connector 265.

The cartridge 25 has an upper section 40 holding the drip chamber 45, and a lower section 47 that can be operable with a flow control mechanism to control a flow rate of fluid to be delivered to the patient. The flow control mechanism can control the flow rate to be within a desired range. In some cases, the flow control mechanism can shut off the flow of the fluid and prevent fluid delivery to the patient.

To control the flow rate, the flow control mechanism can include a clamp mechanism. The lower section 47 can include the clamp mechanism and mounting elements. The clamp mechanism alone, in some implementations, controls the flow from the infuser 10. The flow control mechanism can alternatively or additionally include a pump mechanism. In such cases, the pump mechanism alone controls the flow from the infuser 10, and in other cases, both the clamp mechanism and the pump mechanism control flow from the infuser.

The cartridge 25 can include features for drop formation. The drip chamber 45 of the cartridge 25 facilitates the formation of fluid drops as medical fluid is delivered from the IV container. The drip chamber 45 can include a drop forming element, such as a drop forming element as will be described with respect to FIGS. 5B and 5C.

The cartridge 25 can be mounted onto the chassis 15. A user may manually eject the cartridge 25 by toggling a cartridge ejector 34. A sensor (not shown) may be included in the chassis 15 to confirm that the lower section 47 of the cartridge 25 is correctly mounted onto the chassis 15 to operate with the drop detector 35 and the flow control mechanism.

In some implementations, the drip chamber 45 can be modified to include additional features for alignment with the drop detector 35. For example, the drip chamber can include etched features around a circumference of the chamber to indicate where along the drip chamber the drop detector can align. The drip chamber may also include printed features for measurement and alignment. In some implementations, the IV container may be attached directly to the flow control mechanism, so that all components are in a single, compact arrangement. In some examples, the flow control mechanism is a separate component that can be attached to the infuser or can be operable with tubing extending from the infuser to control the flow of fluid from the infuser to the patient. In some implementations, the load connector may further include a hook to easily hang an IV container. While the cartridge is described to include a lower section and an upper section separated by the drip chamber, in some implementations, the lower and upper sections could be a single component. For example, the cartridge may include a rigid structure connecting the two sections that also accepts the drip chamber.

In some implementations, chassis 15 may include one or more features to orient a fluid line from the IV container to the top of the drip chamber. These features can ensure that the fluid line approaches the drip chamber by going across the top of the infuser. The features can also guide the fluid line such that the fluid line does not kink. For example, the chassis can have a clip disposed on the opposite side of the cartridge that accepts the fluid line. The fluid line can further have a feature that locks into the clip in substantially a single orientation. In particular, the feature can ensure that the fluid line, as it comes from the IV container, enters the bottom of the clip and exits the top of the clip. The clip can further contain a switch or sensor that indicates whether the fluid line has been properly inserted into the clip.

Infuser Cartridge

Figure 2A:
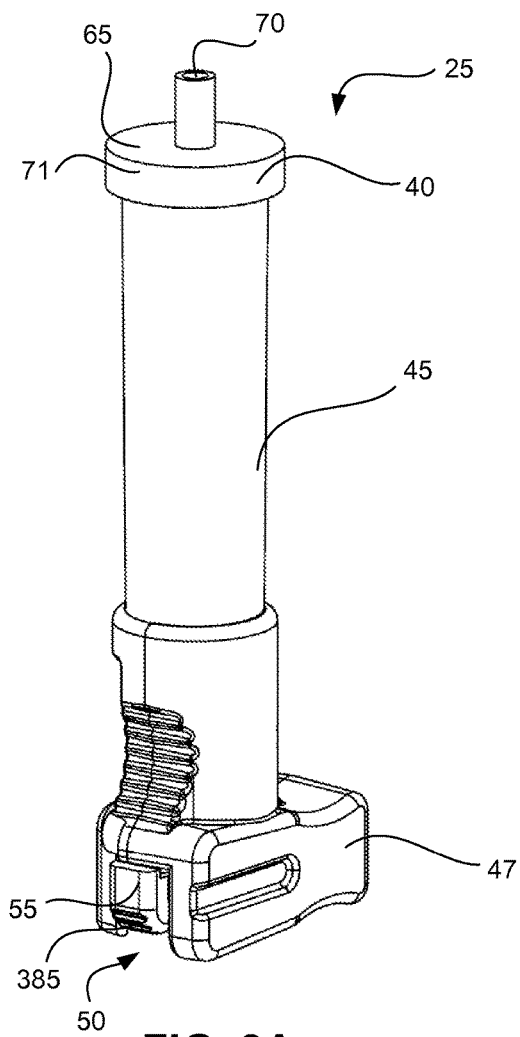
FIGS. 2A and 2B are the front and rear perspective views, respectively, of an example of a cartridge of the infuser shown in FIG. 1A.
Figure 2B:
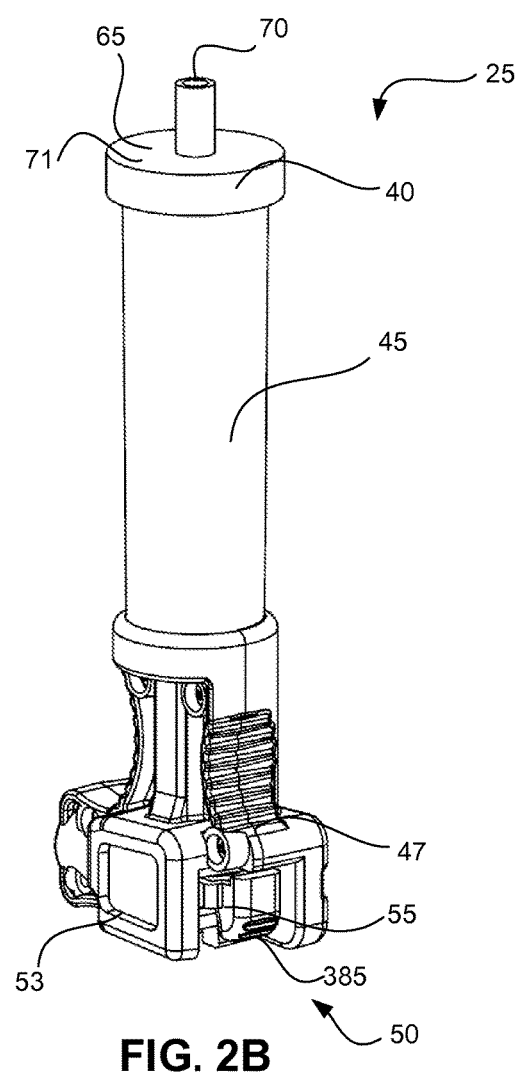

FIGS. 2A and 2B, show front and rear, respectively, perspective views of infuser cartridge 25. In the examples of FIGS. 2A and 2B, the infuser cartridge 25 (also referred to herein as the "cartridge") incorporates the drip chamber 45. The infuser cartridge 25, in some examples, includes portions of the flow control mechanism that controls delivery of the medical fluid from the drip chamber 45 through tubing to a patient. In the example shown in FIGS. 2A and 2B, the cartridge 25 includes a movable clamp element 55 that composes a part of the flow control mechanism. The clamp mechanism 50 functions as a valve to control the amount of fluid delivery from the drip chamber 45 through the flow control mechanism. The clamp mechanism 50 can clamp on the tubing extending from the drip chamber 45 to cause to occlude the tubing such that fluid cannot be delivered from the drip chamber 45.

In some implementations, instead of or in addition to the clamp mechanism 50 of the infuser cartridge 25, the flow control mechanism may include a pump mechanism that is disposed in or associated with the housing. The pump mechanism can pump the medical fluid from the drip chamber 45 to the patient, for example by engaging with an exposed length of the tubing conduit that is located between the drip chamber and the outlet end of tubing. The pump mechanism can include, for example, a positive displacement pump, such as a linear peristaltic pump of the type which secures a length of standard tubing conduit between peristaltic fingers and a pressure plate by means of a hinged door.

With regards to the clamp mechanism 50, the lower section 47 of the infuser cartridge 25 is sealed to the drip chamber 45 to fit tightly enough that the cartridge 25 will not move relative to the drip chamber 45. The sealed engagement between the lower section 47 and the cartridge 25 further can help to maintain sterility of the fluid pathway and to prohibit fluid leaks. The lower section 47 and upper section 40 of the infuser cartridge can be made of a rigid material, such as a reinforced polymer, to provide a structure that a user can easily manipulate and handle.

The drip chamber 45 has surfaces generally exposed on the front (FIG. 2A) and rear (FIG. 2B), which can provide users easily accessible surface for handling the cartridge 25. Along the side of the lower section 47 of the cartridge 25 are mounting surfaces 53 that provide accurate alignment with the infuser and allow the cartridge 25 to be locked in place. The clamp mechanism 50 can be operated (i) automatically to control flow in response to readings from sensors on the infuser or (ii) manually so that a user can prime the tube set or stop the flow in the event of an emergency. The clamp mechanism includes a movable clamp element 55 that provides a manual engagement surface 385 for the clamp mechanism 50 when the cartridge 25 is not mounted in the infusion device. A user may slide the manual engagement surface 385 to manually disengage the clamp mechanism 50. The upper section 40 includes a cap 65, which provides an inlet 70 to connect tubing from the IV container. During use, medical fluid from the IV container drips from the inlet 70 and falls through the drip chamber 45 toward the lower section 47 of the cartridge 25. The cap 65 can include a top alignment feature 71 so the cartridge 25 can securely sit within the chassis of the infuser.

Figure 6A:
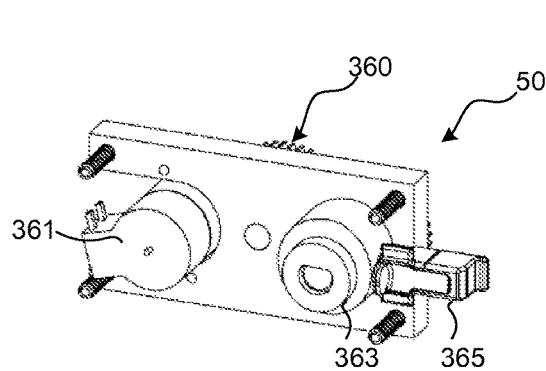
FIGS. 6A and 6B are front and rear perspective views, respectively, of an example of a portion of a flow control mechanism included on a chassis of the infuser in FIG. 1A.
Figure 6B:
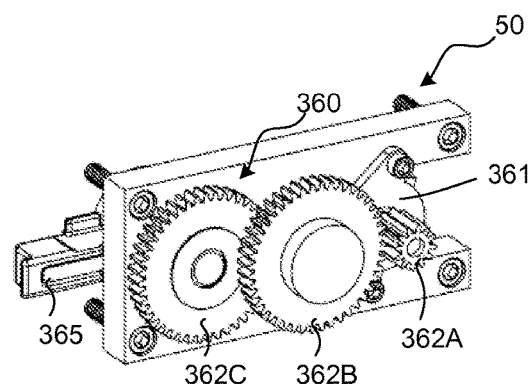
Figure 6C:
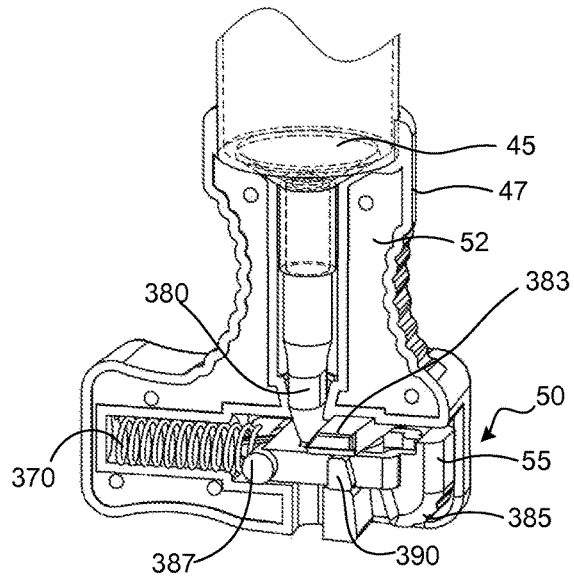
FIG. 6C is a rear perspective view of an example of the portion of the flow control mechanism of FIGS. 6A and 6B included on a lower section of the cartridge of FIG. 2A, with a rear portion of the lower section of the cartridge removed.
Figure 6D:
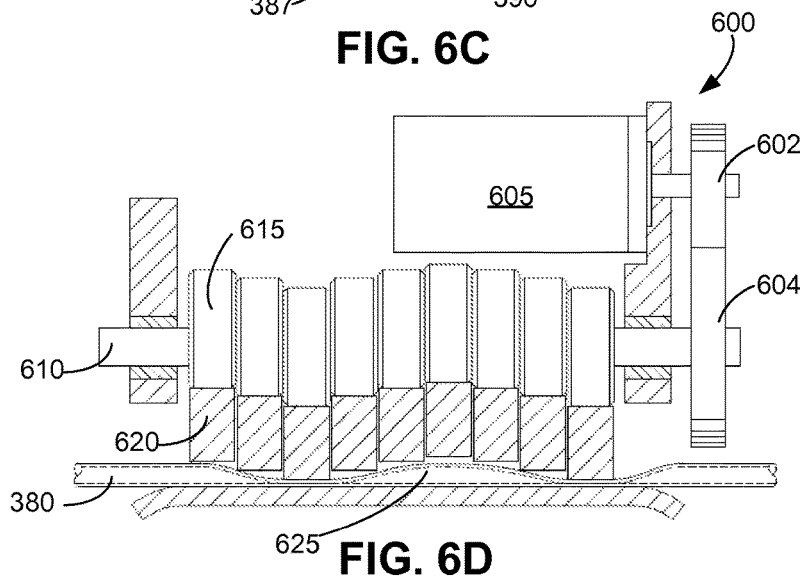
FIG. 6D is a front cross-sectional view of another example of a flow control mechanism for the infuser in FIG. 1A.

As described herein, in some examples, the flow control mechanism can include both the clamp mechanism 50 as well as a pump mechanism (e.g., a linear peristaltic pump 600 of FIG. 6D). In response to, for example, an emergency shut-off situation, the clamp mechanism 50 can control the flow by shutting the flow off to prevent further fluid delivery. The pump mechanism can function to control the flow within the desired range when the infuser operates normally.

In some implementations, the cartridge 25 is manufactured such that the drip chamber 45 is a non-removable component. While the lower section has been described to be sealed to the drip chamber, the lower section and the drip chamber can alternatively be clamped or snapped together.

In some implementations, the drip chamber 45 and the tubing extending from the drip chamber 45 is a separable and removable component of the cartridge 25. During use, the drip chamber 45 with the tube is inserted into the lower section 47 of the cartridge 25 and then locked in place. For example, the drip chamber 45 can be inserted into the lower section 47 and mate to a top portion of the lower section 47 to join the lower section 47 with the drip chamber 45. The lower section 47 can include a latching mechanism that enables the tubing of the drip chamber 45 to be inserted into the lower section 47.

Electrical Connections of the Elements of the Infuser

Figure 3:
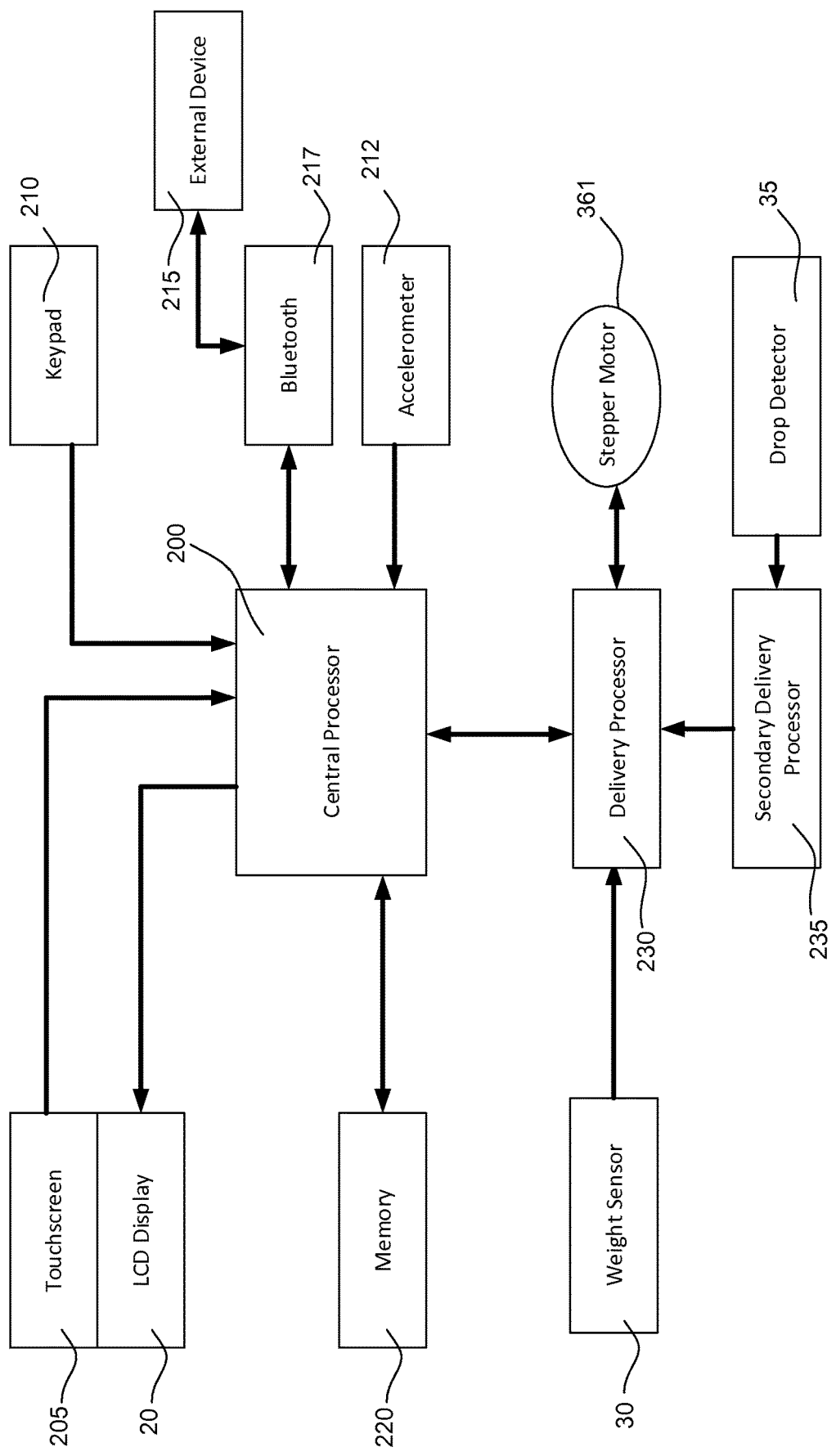
FIG. 3 is a block diagram of components of the infuser of FIG. 1A.

FIG. 3 is a block diagram illustrating an example interconnection of electrical components of the infuser. In some implementations, at least some of the components may be included on a single printed circuited board that includes, for example, a microcontroller, voltage regulators, motor driver components, display driver components, and wireless communication components. The infuser may include a central processor 200 that receives inputs from a display 20 with a touchscreen 205, a keypad input 210, an accelerometer 212 attached to the display 20, an external device 215 such as a personal computer or tablet device via a Bluetooth® transceiver 217, a memory storage element 220, and a delivery processor 230.

The delivery processor 230 is operable with the weight sensor 30, the drop detector 35 via a secondary delivery processor 235, and a stepper motor 361. The delivery processor 230 may receive weight information for the IV container hung on the weight sensor 30 as well as drop count information from the drop detector 35. The secondary delivery processor 235 may receive a signal when the drop detector 35 has detected a drop of medical fluid. The secondary delivery processor 235 can therefore receive several signals corresponding to the drops of the medical fluid through the drip chamber. The delivery processor 230 can receive corresponding signals from the secondary delivery processor 235 or directly from the drop detector 35. The combined use of information collected from these two sensors 30, 35 will be elaborated below with respect to FIG. 13.

The central processor 200 delivers outputs to the display 20, the external device 215, the memory storage element 220, and the delivery processor 230. The delivery processor 230 in turn can deliver output signals to the stepper motor 361 to control fluid delivery using the flow control mechanism, which is described below in more detail with respect to FIGS. 6A to 6D. In some implementations, the delivery processor 230, instead of or in addition to delivering the output signals to the stepper motor 361 to control the fluid delivery, delivers the output signals to a positive-displacement pump or to a stepper motor that drives the positive-displacement pump. The delivery processor 230 can deliver output signals to the stepper motor 361 to control the clamp mechanism to shut off fluid delivery. The delivery processor 230 can deliver output signals to the positive-displacement pump to control fluid delivery to be within a desired flow rate.

The keypad input 210 has an on/off switch and an emergency stop switch that allows a user to override other instructions from the central processor 200. The accelerometer 212 on the display 20 determines the position of the display 20 and can adjust the visual format of information shown on the display depending on the orientation of accelerometer 212. For example, if the user rotates the display sideways, the accelerometer 212 detects the change in orientation and can modify the display so that the user sees information displayed in a convenient orientation.

The memory storage element 220 may include a library of medical fluids, such as drugs and salt solutions. Each entry into the library may further have a set of physical parameters of the fluid, such as specific weight, specific gravity, viscosity, surface tension, and opacity (e.g., transmissibility of the fluid to light, such as infrared light). Each entry can further include empirical data concerning drop size as a function of fluid flow rate, when the fluid is flowing through a drip chamber containing a particular size of a drop forming element. With access to information about the physical parameters of the particular fluid being infused, the central processor 200 can be programmed to accurately predict the drop volume for a given medical fluid adjusted for the size of the drop forming element in the particular cartridge being used, and also adjusted for the fluid flow rate. In some implementations, the user uses the touchscreen 205, the keypad input 210, or some other appropriate user interface device to select an entry in the medical fluid library. The central processor 200 can then compute the drop volume per drop of the medical fluid based on the parameters of the entry selected by the user.

The memory storage element 220 may further include default settings for the infuser. The user may be able to change these default settings via the display 20 or via the external device 215, or may be able to load default settings into memory storage element 220 as an extension or component of the medical fluid library. The default settings may include configurations of the device, optimized to accommodate modes of medical therapy delivery associated with a particular medical fluid or associated with a particular condition or diagnosis of a patient. The default settings may be customized by a user and electronically loadable into the device. The modes of therapy may include, for example, weight based infusion, continuous infusion, bolus infusion, intermittent infusion, infusion protocols where fluid flow rate varies with time according to a predetermined schedule, infusion protocols where fluid flow rate varies in real time in response to a control signal from a remote device, computer-controlled infusions, and the like. The external device 215 may collect data received by the central processor 200 or can enable the user to monitor statuses of components of the infuser. The delivery processor 230 receives data from the weight sensor 30 and the drop detector 35 and, as will be described later, may use that data to make a determination of the amount of fluid to deliver using the flow control mechanism, e.g., the clamp mechanism or the positive displacement pump. The secondary delivery processor 235 may further drive an infrared (IR) light-emitting diode (LED) of the drop detector 35.

While the medical fluid library has been described to include medical fluid parameters known in the art, such as viscosity or specific gravity, the medical fluid library may also include empirically derived values. For example, drop size may vary according to changes in flow rate of the specific medical fluid being delivered. The drop size may vary depending on size and dimensions of a drop forming element of the drip chamber. For a particular medical fluid flowing through a particular drop forming element, an empirically derived scaling factor can be applied to the flow rate to compensate for nonlinear changes. In some implementations, the functionalities of the delivery processor 230 may be implemented using the central processor 200.

While a Bluetooth transceiver 217 is described, any means of wired or wireless communication with an external device can be used to transfer information to and from the central processor. For example, a wireless transceiver such as a WiFi transceiver, or an external transceiver connected to a port (e.g., a Universal Serial Bus (USB) port) may also be used. In addition, while an external device is shown, the infuser may be operable without the cooperation of any external device.

The components may also include additional mechanical position encoders and sensors connected to the central processor 200. For example, the clamp mechanism may include a rotary encoder on its motor, which will be described in more detail with respect to FIGS. 6A to 6D, to determine the extent to which the clamp mechanism has been actuated. The drip chamber may also have a fluid level detector to determine the amount of fluid stagnant in the drip chamber. The controller can perform other functions, such as monitoring limits or variations in the count values. A dedicated hardware counter can also be used and connected to some external processor. In examples in which the infuser delivers medical fluid using the positive displacement pump, a motor of the peristaltic pump can include a rotary encoder or Hall effect sensor, to monitor the speed of the motor and the flow control mechanism.

In some implementations, the central processor 200 is part of an infuser that includes the drop detector 35, the weight sensor 30, and other components shown in FIG. 3. The central processor 200 can alternatively be separate from the drop detector 35 and the weight sensor 30. The drop detector 35 and the weight sensor 30 can be modular components that can be connected to and disconnected from the central processor 200. In some examples, the flow control mechanism is also a modular component separate and independent from the weight sensor 30, the drop detector 35, and the central processor 200.

Weight Sensor

The weight sensor 30 detects the weight of the IV container used during treatment. The sensor can generate an electrical signal in response to an electrical parameter that corresponds to the weight of the IV container. The weight sensor 30 includes transducers that convert a force exerted by the load of the IV container into one or more electrical parameters. Examples of the electrical parameters include, inductance, resistance, capacitance, frequency, or another parameter generated by the transducers.

Figure 4A:
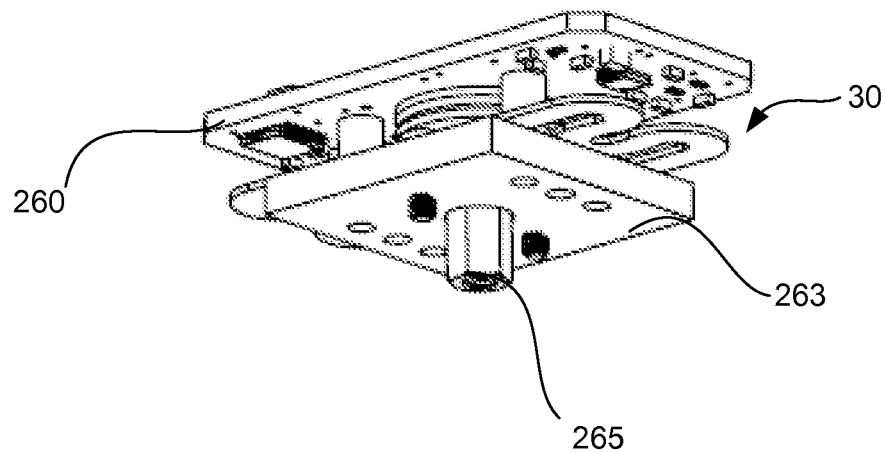
FIG. 4A is a bottom perspective view of an example of a weight sensor.
Figure 4B:
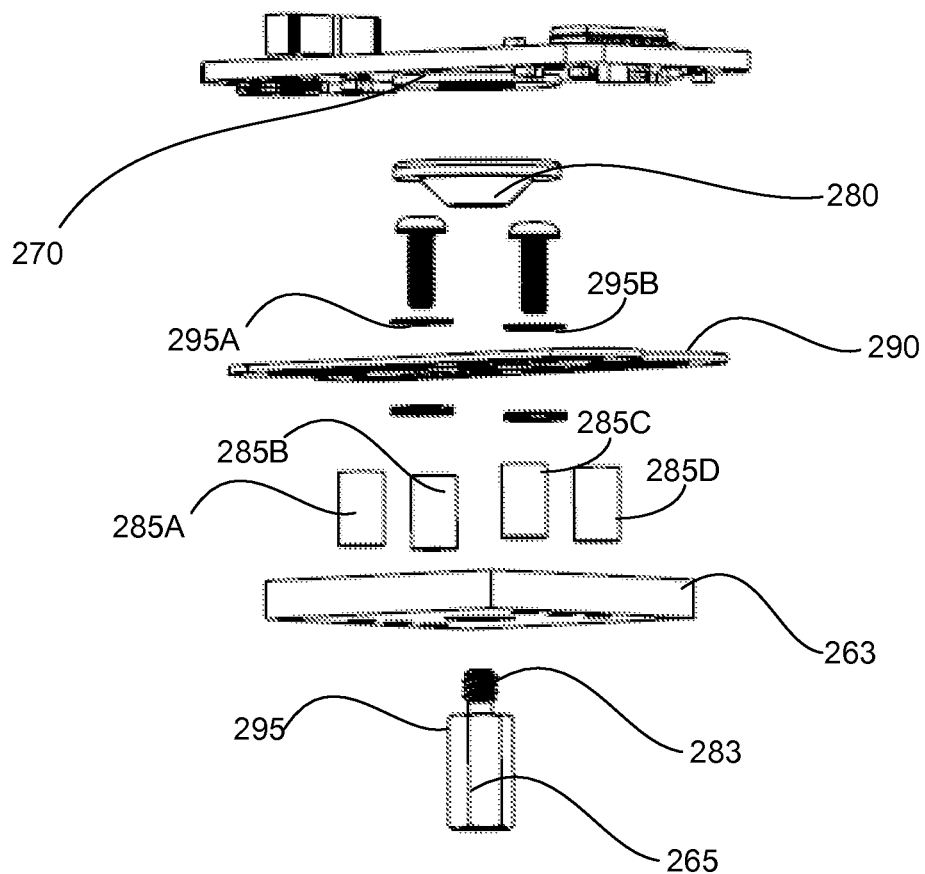
FIG. 4B is an exploded front perspective view of the weight sensor of FIG. 4A.

FIGS. 4A to 4E depict an example of the weight sensor 30 in which the weight sensor 30 includes a circuit having an inductance that varies in accordance with the load on the weight sensor 30. In some example, the circuit can include an inductive component such that the inductance of the component varies substantially proportionally to the load on the weight sensor. FIG. 4A shows a bottom perspective view of an example of the weight sensor 30. FIG. 4B shows an exploded front perspective view of the weight sensor 30. Referring to FIGS. 4A and 4B, the weight sensor 30 includes a printed circuit board 260.

Figure 4C:
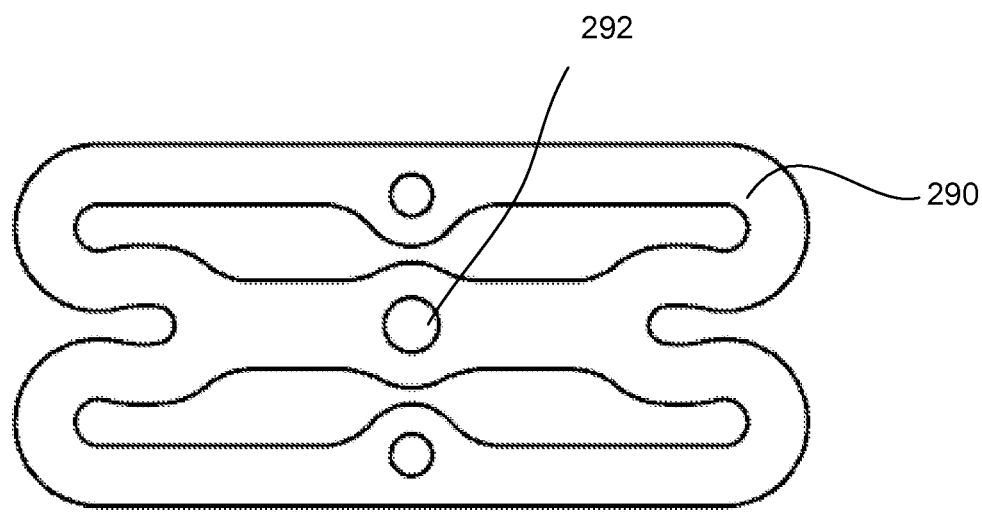
FIG. 4C is a top view of an example of a spring element of the weight sensor of FIG. 4A.

In some implementations, the weight sensor includes a tank circuit. For example, the weight sensor 30 can include a coil 270 an inductance of which changes due to a weight or load placed on the load connector 265. Therefore, the coil 270 forms a portion of a tank circuit, an oscillation frequency of which changes with the weight. The weight can therefore be determined as a function of the oscillation frequency of the circuit. The inductive coil 270 is flat, has an air core, and is fixed to the lower surface of the circuit board 260. A target 280 is a flat conductive element attached to the top center of a flat spring 290. FIG. 4C shows an exemplary flat spring 290 that has geometry to achieve a certain amount of deflection at a given load at a load connector attachment point 292. For example, for heavier IV containers, the flat spring may be desired to be have greater structural stiffness by adding material. In some implementations, the flat spring may be made of an elastic such as stainless steel, spring steel, or aluminum.

Figure 4D:
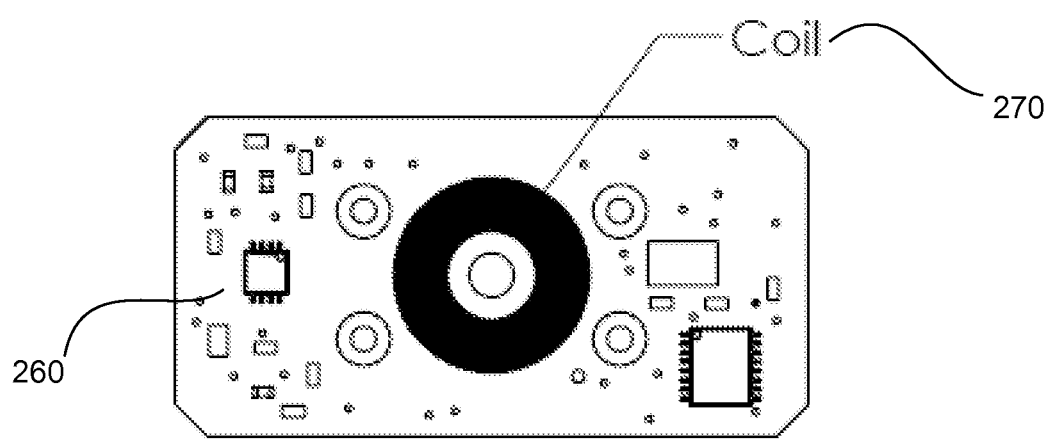
FIG. 4D is a bottom view of a coil and a printed circuit board of the weight sensor of FIG. 4A.

FIG. 4D shows an example of the coil 270 attached to the bottom of the printed circuit board 260. In the example as shown, the coil 270 is an etched spiral pattern in the copper surface of the circuit board. The target 280 has a tapped center hole that mates with a threaded portion 283 of the load connector 265. As a result, the target 280 and connector 265 are coupled together. The circuit board 260 is mounted a fixed distance above the support plate on spacers 285A to 285D. The sizes of the coil 270, target 280, spacers 285A to 285D, spring 290, and spacer washers 295A, 295B are set such that there is initially a small gap between the target 280 and the coil 270. The small gap prevents electrical current from flowing from the coil 270 into the target 280.

The spring 290 is a stiff linear spring such that displacement of the spring 290 will be proportional to an applied force. A load applied to the load connector 265 stretches the spring 290, which in turn causes a displacement of the target 280. The support plate 263 can be positioned to limit the maximum deflection of the spring 290 so that an excessive load will not damage the spring 290. In the event of a compressive load, the load connector 265 has a wide portion 295 that causes the load connector 265, and thereby the spring 290, to stop against the support plate 263. The spring 290 is protected from excessive distortions that might change its characteristics, and the coil 270 is protected from being struck by the target 280. The flat spring 290 can be fabricated using a water-jet or chemical etching process on ground spring stock. The coil 270 may be fabricated by a standard coil winding process with insulated conductive wire, such as copper or aluminum.

While the coil has been described as a component separate from the printed circuit board, in some implementations, the coil may be fabricated as part of the circuit board making process. In that case the coil can be an etched spiral pattern in the copper surface of the circuit board. For greater inductance, stacked coils may be constructed on multiple layers of the printed circuit board, and connected in series using vias on the board. Further, other implementations can employ different spring types such as coil springs of leaf springs. The configuration of components can also be modified so that compressive rather than tensile forces can be measured. While the infuser has been described to include the weight sensor, in some implementations the infuser and the weight sensor can be mounted separately from the cartridge mount, display, and other hardware. The weight sensor could communicate with the control electronics, which will be explained in more detail, using a connecting cable or wireless link. In some implementations, the support plate may include features to fix the infuser to a support structure, such as an IV pole.

Figure 4E:
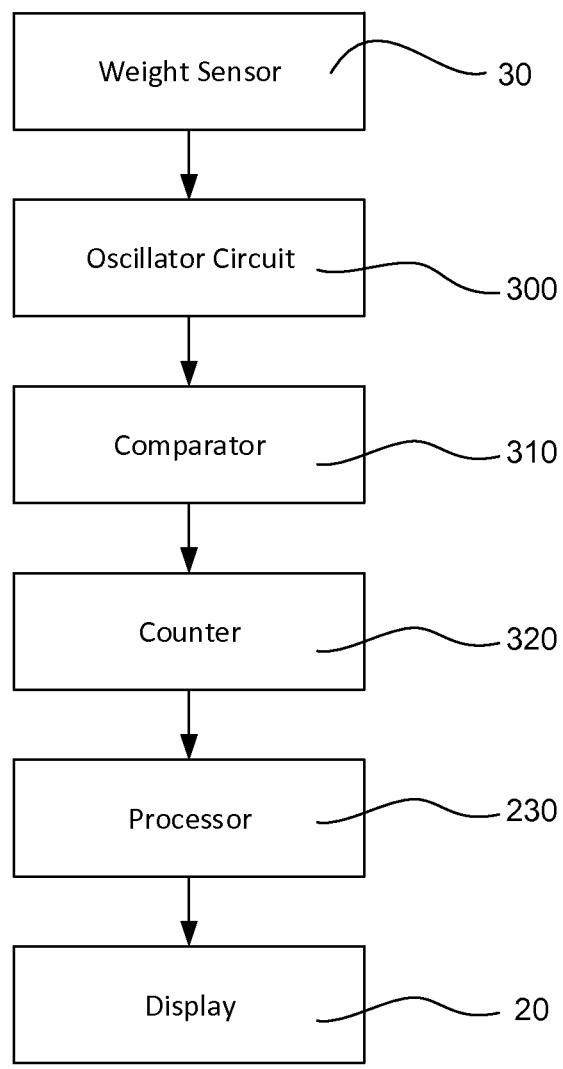
FIG. 4E is a block diagram of a relative arrangement of an electronic circuit of the weight sensor of FIG. 4A.

FIG. 4E is a block diagram of a relative arrangement a weight sensor circuit for detecting the weight to displaying the information. The printed circuit board 260 includes several components to measure the change in inductance of the coil. In the example of FIG. 4E, the weight sensor 30, which includes the coil, is connected to a one or more capacitors on the circuit board to form a resonant "tank circuit". Additional elements are added to make the resonance into a self-sustaining oscillator 300, such as a Colpitts oscillator circuit. Referring to FIG. 4A to 4E, in the above described configuration, the inductance of the coil 270, and thus the oscillating frequency, is dependent on the distance of the target 280 to the coil 270. The alternating magnetic fields in the coil 270 produce eddy currents in the conductive target 280 that increase the coil 270 inductance. This effect decreases as the target 280 to coil 270 distance increases. As the applied force increases, the target 280 is pulled away from the coil 270, decreasing the inductance and thus increasing the frequency of the oscillator 300. Typical oscillation frequencies may be in the range of 0.5 to 5 MHz. The output from the oscillator 300 may pass through a comparator 310 so that a pulse counter 320 can measure the frequency of the oscillator 300.

The counter 320 can be an asynchronous counter that can be incremented by an external signal. The counter 320 can be, for example, part of the secondary delivery processor 235 that has a crystal-controlled clock for accurate timing. A program on the secondary delivery processor 235 zeroes the counter 320, starts the counter 320 (counting the number of oscillator cycles), delays for a fixed time, stops the counter 320, and reads the counter value. The secondary delivery processor 235 can then compute the frequency as the number of cycles divided by the fixed counting time. The infuser can be calibrated to determine a relationship between frequency/counts and applied load (i.e., weight of the IV bag). After processing the information received from the weight sensor, the secondary delivery processor 235 can deliver the information (via the central processor described earlier) to the display 20.

While a Colpitts oscillator is described, other variations, such as a Hartley or Clapp oscillator, can also be used. In some implementations, the relationship between the oscillator frequency and the weight is somewhat nonlinear, and so calibration values may have to be determined at three or more points. An algorithm, such as an Nth order polynomial function or more simply a lookup table, can be implemented on the controller to convert the oscillation counts to force values. In some implementations, the counter can be run until it overflows. The count range can be adjusted by pre-loading a starting value into the counter. In this case the controller first zeroes an internal timer that is coupled to the crystal time base. This timer and the oscillator counter are started together. When the oscillator counter overflows the controller is signaled to stop and read the internal timer. In this example, the time for a given number of counts is measured, rather than the number of counts in a fixed time. The counting method can be chosen to best fit the selected controller and counting hardware. Further, in other implementations, the size and thickness of the spring can be adapted to operate over a wide range of forces so that the infuser can accept a variety of sizes for IV containers.

In some implementations, the oscillator counting period can be splits into a number of shorter periods with little or no loss of resolution. The counts for the individual periods can be added together to get the full period count. In such cases, a controller or dedicated counter with a small counting range (i.e., 16 bits rather than 24 bits) can be used to capture the counts for the shorter periods. The individual counts also can be compared to determine whether the load is changing or if there is other instability during the overall counting period.

Components employed in the weight sensor circuit can exhibit temperature dependence. Accordingly, a device used over a range of temperatures may be configured to compensate for temperature variations. For example, selection of components in the oscillator circuit can mitigate temperature effects. Further, a temperature sensor can also be connected to the controller so that additional compensation can be provided by software or firmware running on the controller. While a single oscillator is described above, for operation under very wide temperature ranges, more than one oscillator circuit with identical coils and capacitors can be implemented. One oscillator would have a fixed distance between the coil and target while the other would vary with load. Measurements could be obtained in one of several ways. The oscillation counts over a fixed time could be simultaneously captured for both oscillators and then compared. Alternatively, one oscillator could provide a time base to measure counts on the other oscillator so as to reduce the effect of most temperature dependencies of the oscillator circuits.

Figures 4F, 4G:
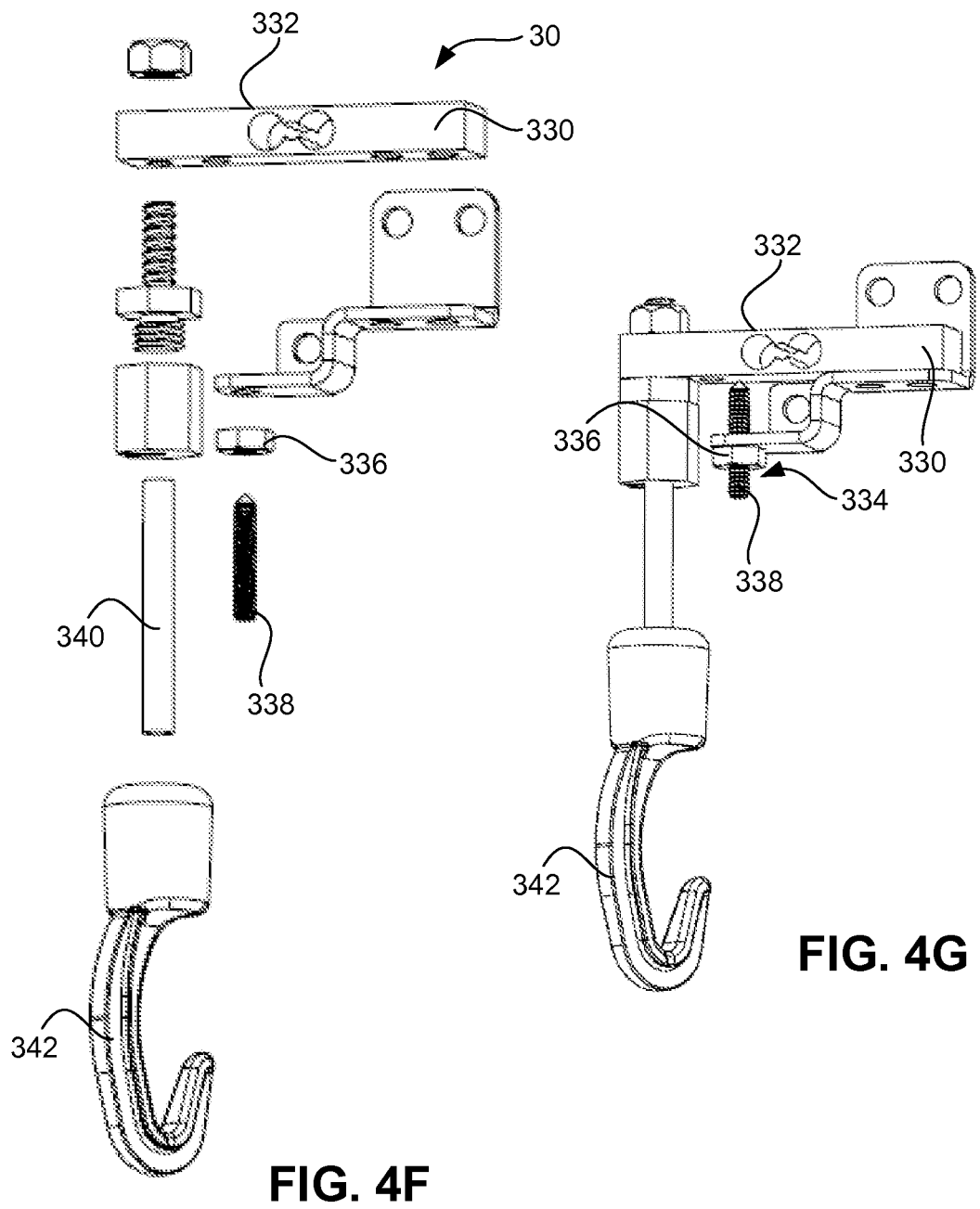
FIG. 4F is an exploded front perspective view of another example of a weight sensor.
FIG. 4G is a front perspective view of the weight sensor of FIG. 4F.

While the example shown in and described with respect to FIGS. 4A to 4E illustrate an inductance-based sensor to detect weight, in some cases, the weight sensor 30 can include a circuit in which an electrical resistance is indicative of the weight of the IV container. FIG. 4F shows an exploded front perspective view of an example of the weight sensor 30 using a beam-type load cell, and FIG. 4G shows an unexploded front perspective view of the weight sensor 30 using the beam-type load cell. In this example, the weight sensor 30 includes a support beam 330. A strain gauge (not shown) is positioned across a top surface 332 of the support beam 330 such that a resistance of the strain gauge changes in response to deflections of the support beam 330 when the support beam 330 bends.

To prevent damage of the weight sensor 30 due to inadvertent excessive loads applied to the weight sensor 30, a stop mechanism 334 can limit the amount of flexure of the support beam 330. The stop mechanism 334 includes, for example, a nut 336 and a headless screw 338. The headless screw 338 contacts the support beam 330 when the support beam 330 bends by a predetermined amount.

A flexible link 340 extends from the support beam 330. A hook 342 at the end of the flexible link 340 can carry a hanging IV container. The flexible link 340 transmits vertical loads to the support beam 330. In some cases, the flexible link 340 flexes under bending, twisting, or side loads to prevent damage to the weight sensor 30 due to various load conditions.

When the hook 342 is carrying a load, such as an IV container, the load causes the support beam 330 to deflect downward. In this configuration, the strain gauge generates an electrical signal indicative of the strain in the support beam 330. The amount of strain is indicative of the weight of the IV container. Therefore, based on the magnitude of the electrical signal, the central processor can determine the weight of the IV container.

Drop Detector

Figure 5A:
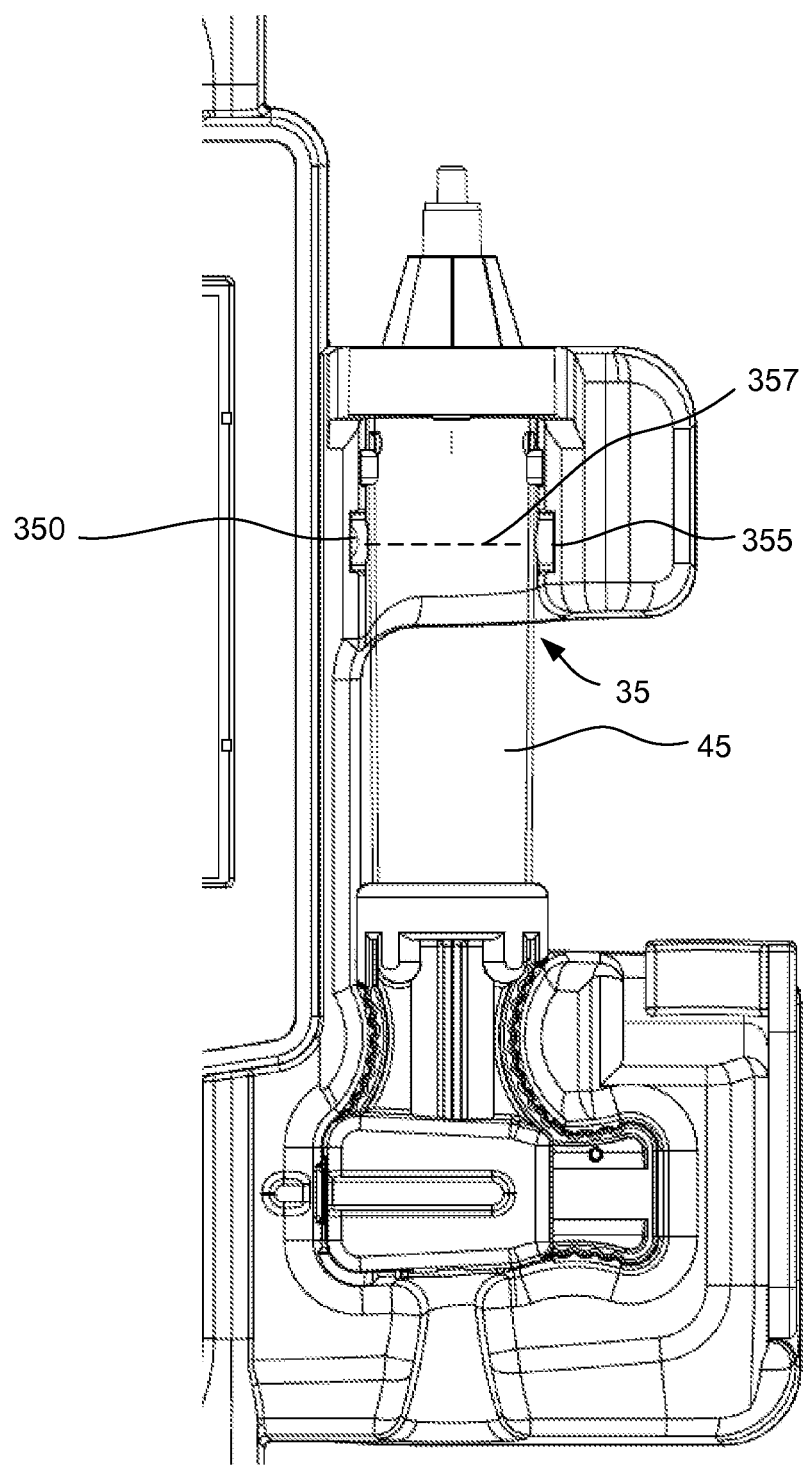
FIG. 5A is a front view of a drop detector of the infuser shown in FIG. 1A.
Figure 5B:
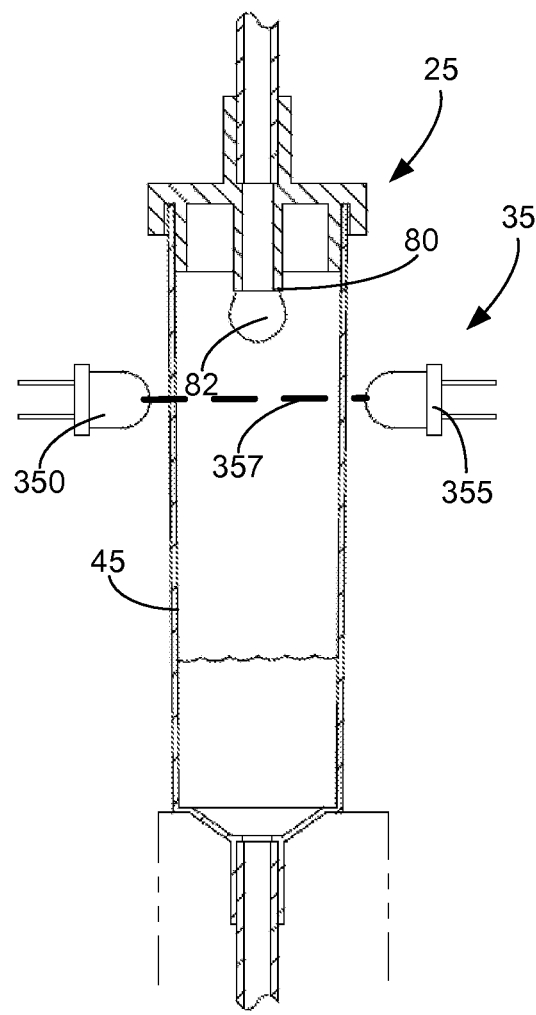
FIG. 5B is a front cross-sectional view of an example of a drip chamber.
Figure 5C:
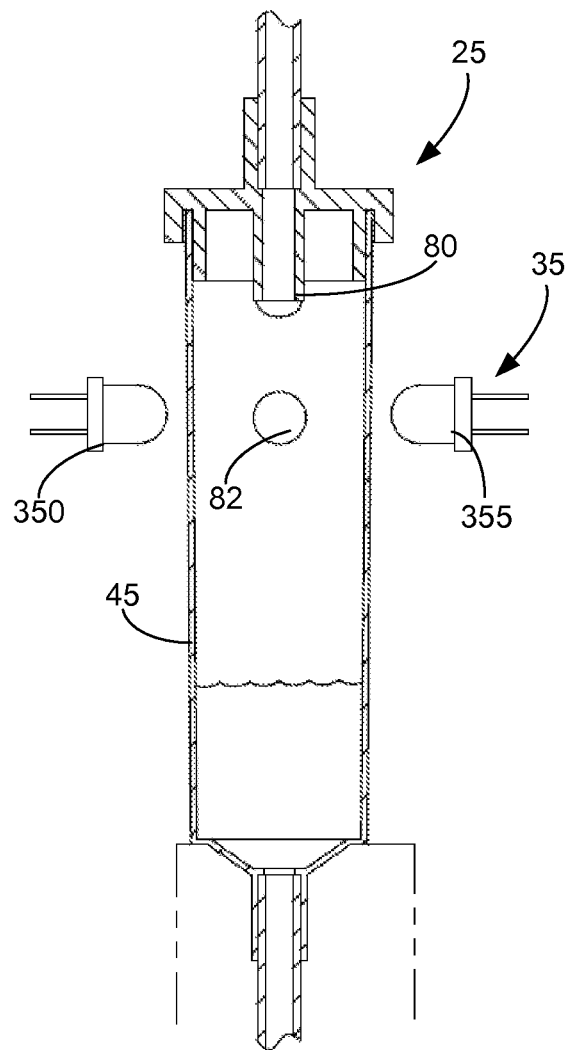
FIG. 5C is a front cross-sectional view of the drip chamber of FIG. 5B, illustrating a fluid drop traversing the drip chamber.

Now referring to FIG. 5A, the drop detector 35 optically detects individual drops of fluid falling in the drip chamber 45. In some implementations, the drop detector includes an infra-red (IR) light-emitting diode (LED) 350 and IR detector 355 placed on opposite sides of the drip chamber 45 and facing each other. The IR LED 350 can be, for example, an Osram SFH 4545 LED that produces a narrow IR beam. The IR detector 355 can be, for example, a Vishay TSSP4038 detector that detects the narrow IR beam. As shown in FIGS. 5B and 5C, the cartridge 25 can include a drop forming nozzle 80 that facilitates formation of a fluid drop 82. The drop forming nozzle 80 can be sized and dimensioned such that drops delivered from the drop forming nozzle 80 have substantially the same size and/or volume.

The fluid drop 82, from the nozzle 80, drops through the drip chamber 45 past the drop detector 35. The drop forming nozzle 80 can be sized and dimensioned such that drops of a given type of fluid delivered from the drop forming nozzle 80 have substantially the same size and/or volume. Each falling drop 82 reduces the illumination of the IR LED 350 on the IR detector 355 as each falling drop 82 falls past an optical path 357 of the IR LED 350. For clear fluids, the illumination reduction is mainly due to refractive effects while for opaque fluids the light is both absorbed and refracted. The drops of the medical fluid can then be delivered to the patient using a flow control mechanism described herein.

The IR LED 350 can be driven by the secondary delivery processor 235 described above in FIG. 3. The secondary delivery processor 235 can be configured to generate a pulse train of programmable duty cycle. Because the drops of a given type of fluid from the drop forming nozzle 80 have substantially similar volumes and sizes, the secondary delivery processor or other processor can determine the volume delivered during a period of time based on the number of drops detected, the type of the fluid being delivered, and the parameters of the drop forming nozzle 80.

While the drop detector is described to include a single IR LED and IR detector, the drop detector can also include a horizontal array of IR detectors employed to detect the illumination of one or more IR emitters. In some implementations of the drop detector, the IR detector has a preference for 38 kHz IR emission with a wavelength of ~850 to ~1050 nanometers (nm) paired with an IR emitter which produces light with a wavelength of about 940 nm. The detectors may be connected to individual controller inputs so that a change in output of any sensor can be measured. Alternatively, the sensors may be wired in a series arrangement into a single controller input. A reduction in illumination at any sensor will cause a corresponding increase in electrical resistance, which can be measured by the controller. The IR LED can be driven by a 38 kHz pulse train and the intensity of the illumination can be variable so as to enable the drop detector to burn through condensation formed on the inside surfaces of the drip chamber. In some implementations, a very high frequency modulation can be applied to the IR illumination and the intensity of the IR illumination is continuously controlled to overcome both noise and masking effects. Further, in some implementations, the IR LED is driven with a high enough power such that it can burn through condensation formed on the inside surfaces of the drip chamber.

Flow Control Mechanism

As described with respect to FIGS. 2A and 2B, the lower section 47 of the cartridge 25 includes a portion of the clamp mechanism 50 to pinch a tube extending from a drip chamber. FIGS. 6A and 6B shows an example of the portion of the clamp mechanism 50 within the chassis 15 that can control flow and, alternatively or additionally, serve as a safety shut-off for the flow of the medical fluid from the drip chamber. FIGS. 6A and 6B are respectively rear and front perspective views of the drive train 360 of the portion of the clamp mechanism 50 contained within the chassis of the infuser, and FIG. 6C is the cartridge 25 portion of the clamp mechanism 50.

Referring to FIGS. 6A and 6B, a stepper motor 361 drives the electronically controllable clamp mechanism 50 in the infuser chassis. The motor 361 drives a series of gears 362A to 362C to reduce the speed and increase the force of the mechanism 50. The third gear 362C is coupled to a cam 363 that engages a linear actuator 365, which in turn presses against the movable clamp element 55 of the cartridge 25 shown in FIG. 6C. A tube 380 passes through the movable clamp element 55. The spring 370 pushes the movable clamp element 55 such that the tube is compressed between the movable clamp element 55 and a fixed clamp element 383. As a result, fluid flow is stopped when the movable clamp element 55 has not been actuated by the clamp mechanism 50. As the linear actuator 365 advances it overcomes the clamping action induced by a spring 370 and gradually opens the tube 380 exiting the drip chamber 45 to allow fluid to flow. The spring 370 can thus bias the movable clamp element 55 so that the tube is closed until the spring force can be overcome by, for example, the force generated by the motor 361. The movable clamp element 55 can further include a manual engagement surface 385 that allows a user to manually disengage the movable clamp element 55 from the tube 380 for priming.

The movable clamp element 55 extends outside of the cartridge and has a manual engagement surface 385 that can be pressed inward against the force of the spring 370. This opens a gap between the clamp elements 55, 383, allowing the tube 380 to open and fluid to flow.

The movable clamp element 55 has a pair of guiding bosses 387 (one is shown in FIG. 6C), projecting from opposite sides of the movable clamp element 55 that slide in grooves (not shown) in the interior surfaces of the cartridge body 52, guiding the linear movement of the movable clamp element 55. A pair of locking bosses 390 (one is shown in FIG. 6C) also projecting on opposite sides of the movable clamp element 55 abut against notches (not shown) on the interior surfaces of the cartridge body 52. When the movable clamp element 55 is slid to its maximum travel position it can then be pressed perpendicular to the sliding direction to lock the movable clamp element 55 into an open tube position. This position can be used for manual priming of the tube 380 and drip chamber 45 or for alternative or additional control of flow with a separate positive displacement or volumetric pump, such as a roller pump. Examples of the alternative or additional control of flow using the positive displacement pump are described herein. Pressing the movable clamp element 55 in the opposite direction releases the locking bosses 390 from the notches and thereby allows the movable clamp element to be slid back into a closed tube position.

In some implementations, the cam rotates approximately 270 degrees with a rise of only about 0.010 to 0.040 inches, providing fine control of the linear actuator movement and the clamp element movement. While a linear actuator has been described to directly drive the movable clamp element, a linear spring can be placed between the two elements. In such an implementation, the spring can provide a compliance so that a large movement of the drive mechanism translates to a small motion but a wide variation in clamping force. The drive resolution can be matched to the spring compliance so that there is adequate force resolution without requiring excessive actuator travel. In other implementations, the clamping mechanism can be designed so that, in case of mechanical failure, the clamping force can only increase. As described above, this can be accomplished with a fixed clamping spring and an adjustable "un-clamping" spring.

While a linear spring has been described to bias the movable clamp element into a closed tube position, other springs known in the art may be employed. For example, the movable clamp element may pivot about a shaft with torsion spring and pivot to a position that compresses the tube.

In some implementations, a force sensor may be placed behind the movable clamping element to measure the amount of force that the movable clamping element is exerting on the tube. The sensed force may be used for control feedback, and a relationship between motor torque and flow rate can be utilized to control the amount of flow based on a motor torque.

In other implementations, a linear encoder on the linear actuator, a rotary encoder on the motor shaft, or a potentiometer attached to the shaft can be implemented to monitor the actuator movement to detect error conditions. While a stepper motor has been described to drive the clamp mechanism, another motor known in the art, such as DC motor or a hybrid stepper analog motor, could be implemented. A simple DC motor could reduce the cost for the motor and electronics.

As described herein, the infuser alternatively or additionally includes a pump mechanism to control the flow of fluid delivered from the infuser cartridge. The pump mechanism can be operated, for example, to control flow in response to readings from sensors on the infuser. The pump mechanism includes, for example, a rotary peristaltic pump, a linear peristaltic pump, or other positive displacement pump. In some cases, the pump mechanism includes a reciprocating piston pump, a rolling diaphragm pump, or a combination of a positive displacement pump and other flow control mechanism. If the pump mechanism includes a positive displacement pump, the pump mechanism can also be deactivated to stop further fluid delivery.

FIG. 6D shows a linear peristaltic pump 600 that pumps fluid through the tube 380 extending from the drip chamber. A motor 605 of the linear peristaltic pump 600 rotates gears 602, 604 to drive a shaft 610 carrying several fingers 620 that engage different portions of the tube 380. The shaft 610 rotates cams 615 each with a corresponding finger 620. Because the tube 380 is compressible, the fingers 620 of the peristaltic pump 600 sequentially compress their respective portions of the tube 380 as the motor 605 drives the fingers 620 of the linear peristaltic pump 600. The linear peristaltic pump 600 acts as a positive displacement pump, as volume delivered from the tube 380 directly depends on the amount of rotation of the motor 605. During a cycle of the linear peristaltic pump 600, the fingers 620 advance a fixed volume in each bolus 625 of fluid delivered through the tube 380.

Other flow control mechanisms can be used with the infusers described herein. Such mechanisms include, for example, syringe pumps, membrane pumps, and peristaltic pumps. Other examples of linear peristaltic pumps that can be used with the infusers described herein are described in U.S. patent application Ser. No. 07/518,987 entitled "Programmable infusion system" filed on May 4, 1990, the entire contents of which are incorporated herein by reference.

The infuser can include combinations of the various flow control mechanisms described herein. For example, the infuser can include the clamp mechanism 50 to perform an emergency shut off valve for the flow of the medical fluid. The infuser can also include the pump mechanism to control the fluid flow rate to be within a desired flow rate.

Latching and Ejection Mechanism

In some implementations, a retaining mechanism and/or an ejection mechanism enable the cartridge 25 to be removably mounted to the chassis 15. The retaining mechanism retains the cartridge 25 in the chassis 15 when the cartridge 25 is mounted to the chassis 15. The ejection mechanism can be actuated to eject the cartridge 25 mounted on the chassis 15. The ejection mechanism releases the cartridge 25 and, in some cases, applies a force to the cartridge 25 to eject the cartridge 25 from the chassis 15. The latching mechanism and the ejection mechanism can be part of a single mechanism that both retains and ejects the cartridge 25.

Figure 7A:
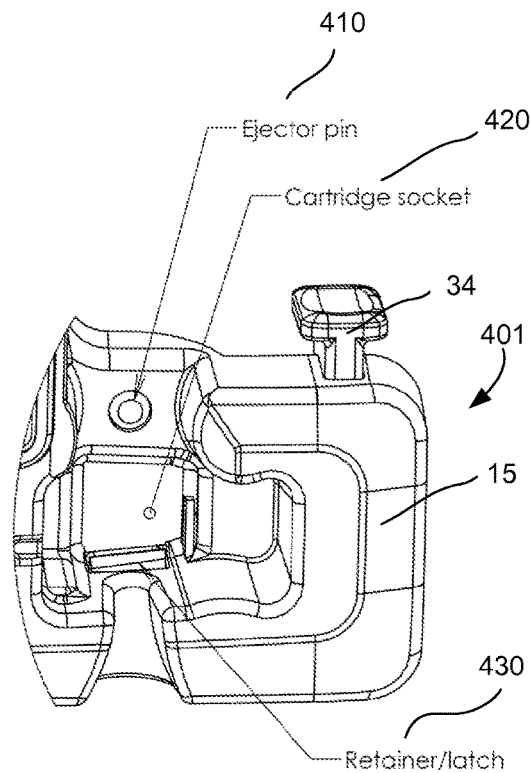
FIG. 7A is an enlarged perspective view of an example of a cartridge socket of the chassis of the infuser of FIG. 1A.
Figure 7B:
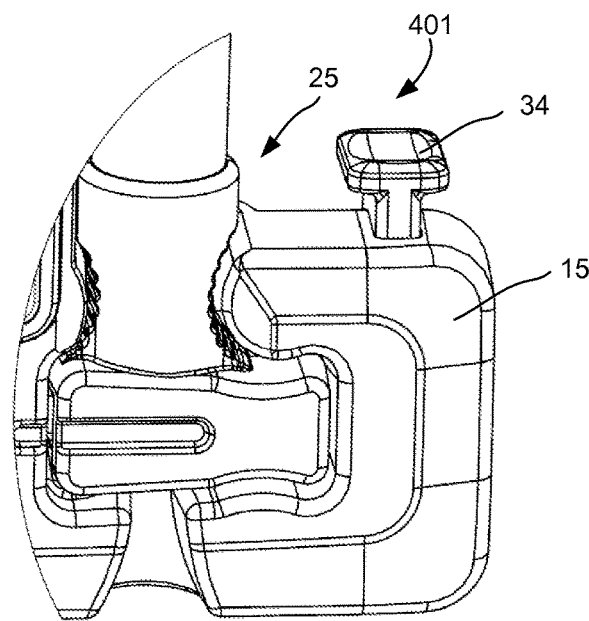
FIG. 7B is an enlarged perspective view of the cartridge socket of FIG. 7A with a mounted cartridge.
Figure 7C:
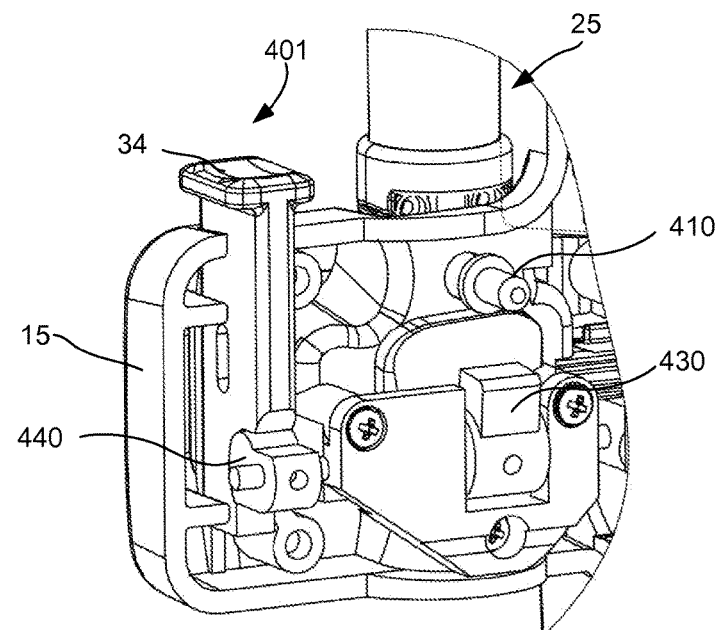
FIG. 7C is an enlarged rear perspective view of an example of a mechanism to eject the cartridge from the cartridge socket of FIG. 7B.
Figure 7D:
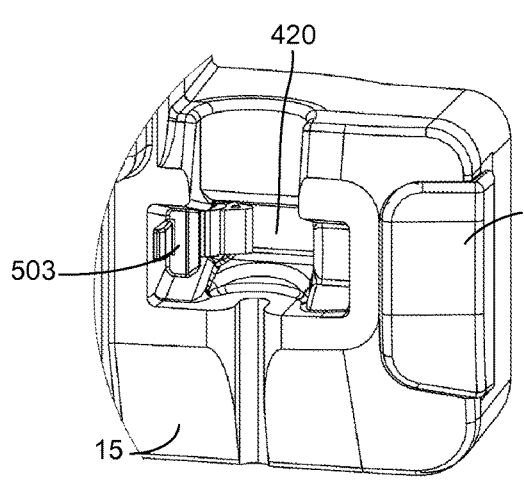
FIG. 7D is an enlarged perspective view of another example of a cartridge socket on the chassis of the infuser in FIG. 1A.
Figure 7E:
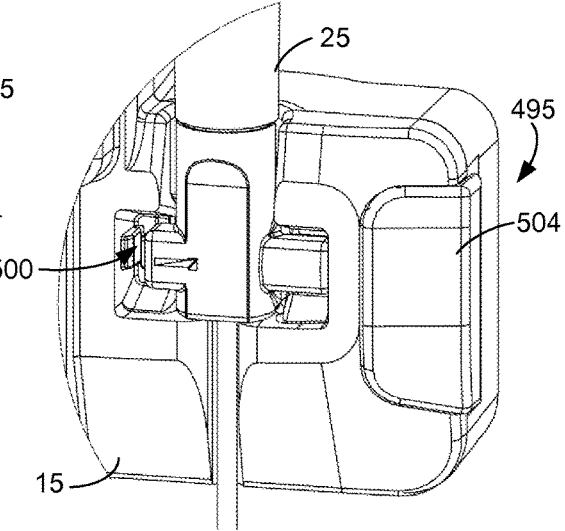
FIG. 7E is an enlarged perspective view of the cartridge socket of FIG. 7D with a mounted cartridge.
Figure 7F:
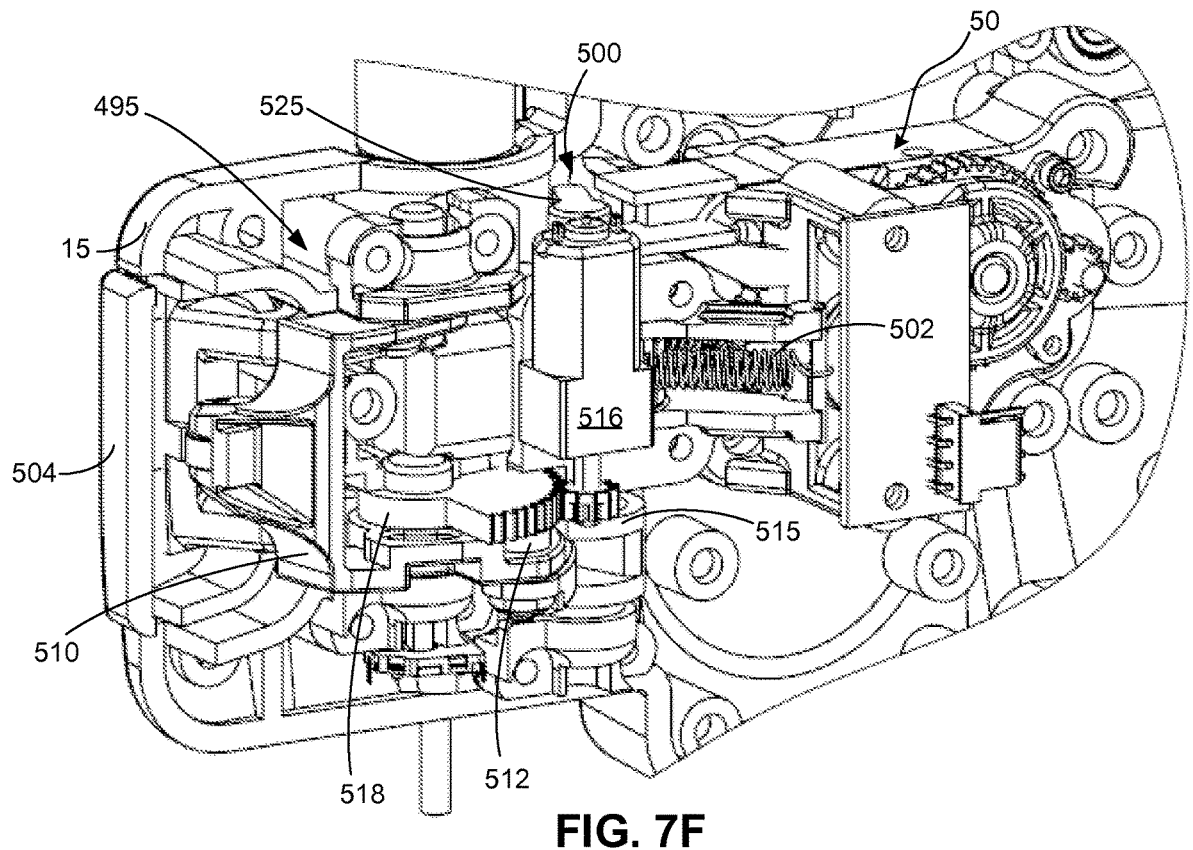
FIG. 7F is an enlarged rear perspective view of an infuser with an example of a retention and ejection mechanism for the cartridge socket of FIG. 7E.
Figure 7G:
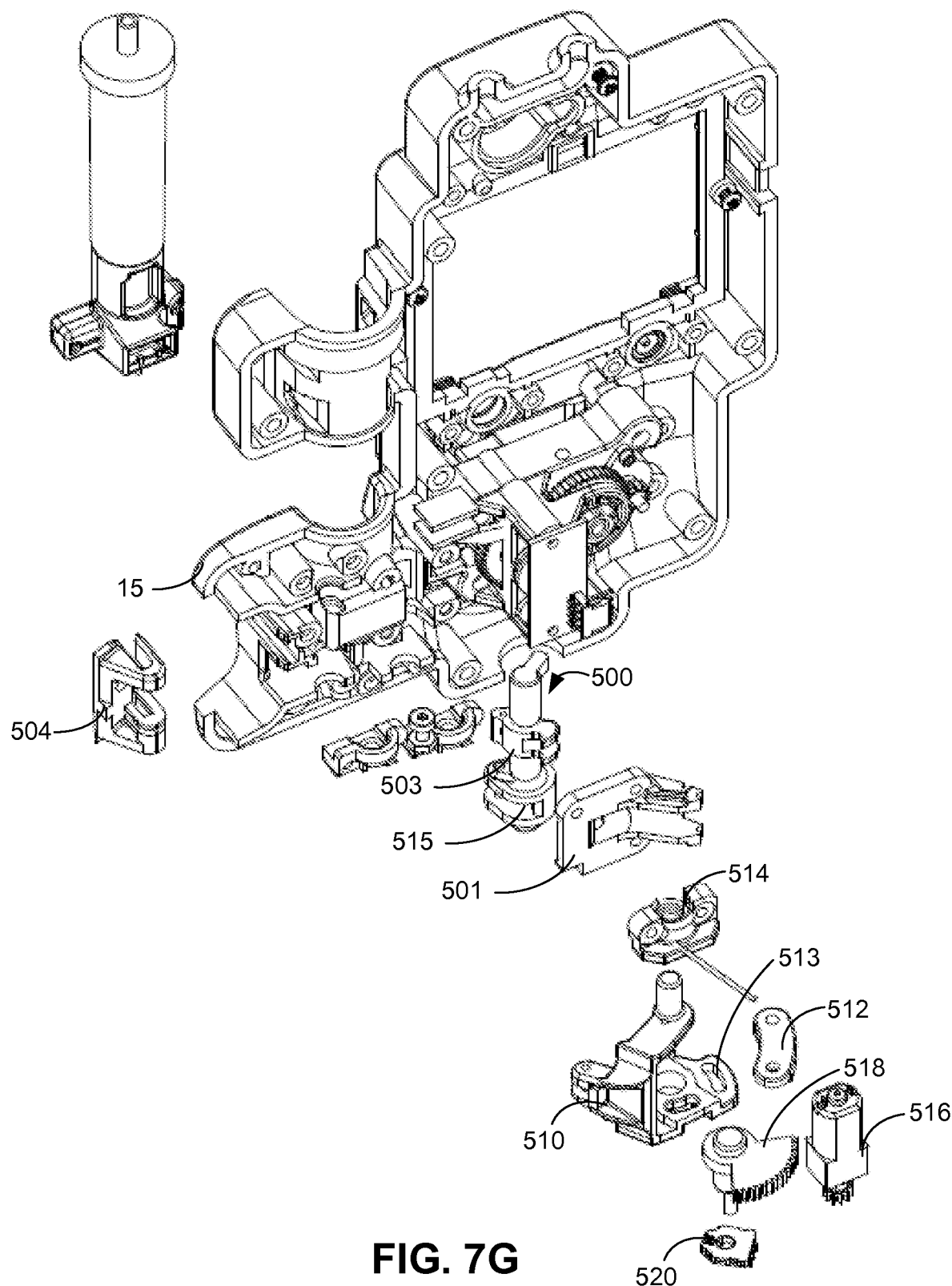
FIG. 7G is an exploded perspective view of an infuser with the retention and ejection mechanism of FIG. 7F.

FIGS. 7A to 7C illustrate an example of a retaining and ejection mechanism 401. FIG. 7A shows the chassis 15 without a cartridge 25. The chassis 15 includes an ejector pin 410, a cartridge socket 420, and a latch 430. The latch 430 enables the cartridge 25 to be inserted into and held on the chassis 15. The ejector 34 is positioned such that actuation of the ejector 34 is a downward motion. The ejector 34 triggers an ejection mechanism that results in disengagement of the latch 430 from a cartridge inserted into the cartridge socket 420. When the cartridge 25 is loaded into the cartridge socket 420, the cartridge ejector 34 can be depressed to trigger the ejection mechanism.

In one example of the ejection mechanism, as shown in FIG. 7C, the cartridge ejector 34 rotates an eject cam 440. The ejector cam 440 is coupled to the latch 430, and rotation of the eject cam 440 results in disengagement of the latch 430 from mounting surfaces of the cartridge 25. The ejector pin 410 can be driven by a spring such that disengagement of the latch 430 causes the spring to press the cartridge 25 out of the cartridge socket 420.

FIGS. 7D to 7I show another example of an ejection and retention mechanism 495. The ejection and retention mechanism 495 is at least partially housed within the chassis 15 adjacent to the clamp mechanism 50. An ejector button 504 of the ejection and retention mechanism is located, for example, on a side surface of the cartridge socket 420. The ejection and retention mechanism 495 can enable a number of operations to eject a cartridge, retain a cartridge, or prevent a cartridge from being inserted into the cartridge socket 420. For example, the ejection and retention mechanism 495 enables a user to insert a cartridge into the cartridge socket 420 to mount the cartridge and to press the ejector button 504 to eject a cartridge. The ejection and retention mechanism 495 also can enable a central processor of the infuser to eject a cartridge in response to an emergency situation (e.g., an infusion outside of safe parameters) or to prevent a cartridge from being inserted into cartridge socket 420.

The ejection and retention mechanism 495 can also be operable with the clamp mechanism 50 described with respect to FIGS. 6A to 6C to enable the clamp mechanism 50 to activate portions of the ejection and retention mechanism 495. In particular, the ejection and retention mechanism 495 and the clamp mechanism 50 can be configured so that activation of the clamp mechanism 50 to shut off flow also causes the ejection and retention mechanism 495 to eject the cartridge.

In some implementations, the ejection and retention mechanism 495 includes a latch 500 that retains the cartridge 25 in the cartridge socket 420 or ejects the cartridge 25 from the cartridge socket 420. The latch 500 is movable between an open position and a closed position. The latch 500 includes a central pivoting tab 503 that protrudes outward from a shaft of the latch 500. The latch 500 is an overcenter linkage, and the tension spring 502 biases the latch 500 toward the open or the closed position. The tension spring 502 is connected to the latch 500 such that, when the latch 500 is between the open position and the intermediate position, the force from the tension spring 502 causes the latch 500 to move toward the open position. When the latch 500 is between the intermediate position and the closed position, the force from the tension spring 502 causes the latch 500 to move toward the open position.

When the latch 500 is in the closed position, the central pivoting tab 503 extends outwardly from the cartridge socket 420 such that central pivoting tab 503 can retain the cartridge 25 within the cartridge socket 420 or enable the cartridge 25 to be inserted past the central pivoting tab 503. When the latch 500 is in the closed position, the cartridge 25 can be inserted past the central pivoting tab 503 of the latch 500 to mount the cartridge 25 to the cartridge socket 420. When inserted, the cartridge 25 causes the latch 500 to move sufficiently to allow the cartridge 25 to move beyond the central pivoting tab 503 without going beyond the intermediate position. The tension spring 502 then biases the latch 500 back toward the closed position to generate a force against the cartridge 25 to retain the cartridge 25 within the cartridge socket 420.

When the latch 500 is in the open position, the central pivoting tab 503 extends outwardly from the cartridge socket 420 such that the central pivoting tab 503 can eject the cartridge 25 from the cartridge socket 420 and/or prevent the cartridge 25 from being inserted into the cartridge socket 420. For example, when the cartridge is mounted in the cartridge socket 420, activation of the ejector button 504 of the ejection and retention mechanism 495 can move the latch 500 from the closed position to the open position to eject the cartridge 25 from the cartridge socket 420. The ejector button 504, when depressed, causes the latch 500 to move to the open position. In the open position, the latch 500 can prevent a cartridge from being inserted into the cartridge socket 420.

The ejector button 504, upon being triggered, actuates a series of links within the chassis 15 that transmits force applied to the ejector button 504 by the user to the latch 500. When the ejector button 504 is triggered, the ejector button 504 applies a force to transfer arm 510 that rotates in a socket within the chassis 15. The transfer arm 510 serves as a lever arm such that the force applied on the ejector button 504 is increased by, for example, 1.5 to 2 times. The transfer arm 510 transmits the force to a linking arm 512 connected to a clevis feature 515 at the bottom of the latch 500. In response to the force, the latch 500 and the central pivoting tab 503 rotate past the intermediate position. The tension spring 502 further biases the latch 500 to the open position. As the central pivoting tab 503 moves toward the open position, it can protrude from the cartridge socket 420 to push a cartridge retained in the cartridge socket 420 out of the cartridge socket 420. In the open position, the central pivoting tab 503 can prevent a cartridge from being inserted and/or retained in the cartridge socket 420.

In some implementations, the linking arm 512 moves freely in an arced slot 513 formed in the transfer arm 510 so that the ejector button 504 can return to an unactuated position after being depressed. A torsion spring 514, for example, supplies a torsional force to bias the ejector button towards the unactuated position.

In some implementations, the user can move the latch 500 from the closed position toward the open position by outwardly pulling on the cartridge 25 when it is disposed in the cartridge socket 420. The outward force from the cartridge 25 can be sufficiently high to cause the latch 500 to move from the closed position toward the intermediate position against the force of the tension spring 502. The latch 500 can rotate a sufficient amount to enable the cartridge 25 to be removed from the cartridge socket 420. In some cases, the amount of movement can be enough to cause the latch 500 to move past the intermediate position. Dismounting the cartridge 25 by manually pulling the cartridge 25 from the cartridge socket 420 can also cause the latch 500 to be moved to the open position, thereby preventing a cartridge from being loaded into the cartridge socket 420.

In some implementations, instead of the force originating from a user depressing the ejector button 504, or a user pulling the cartridge 25 away from the cartridge socket 420, the cartridge socket 420 contains an ejector motor 516 connected to a partial gear 518. Activation of the ejector motor 516 actuates the partial gear 518. The partial gear 518 applies a rotational force on the transfer arm 510 to then rotate the latch 500 to the open position. The latch 500 rotates from the closed position to the open position to cause an ejection of the cartridge 25 independent of the ejector button 504.

A potentiometer 520 can be operable with a shaft driving the partial gear 518 to generate an electrical signal usable by the central processor to determine a position of the partial gear 518. The central processor can use the position, for example, as negative feedback, to control the set point of the ejector motor 516 to rotate the partial gear 518 (e.g., using a proportional-integral-derivative control system).

In some examples, the latch 500 further includes a keyed portion 525. The keyed portion 525 is keyed to a linking arm that interlocks with the clamp mechanism 50. When the clamping mechanism 50 is activated to prevent flow through the tube 380, the activated clamping mechanism 50 also locks the latch 500 such that a cartridge cannot be loaded into the cartridge socket 420. The clamp mechanism 50 can lock the latch 500 in the open position so that when the user attempts to load the cartridge 25 into the cartridge socket 420, the cartridge 25 cannot be retained within the cartridge socket 420.

Figure 7H:
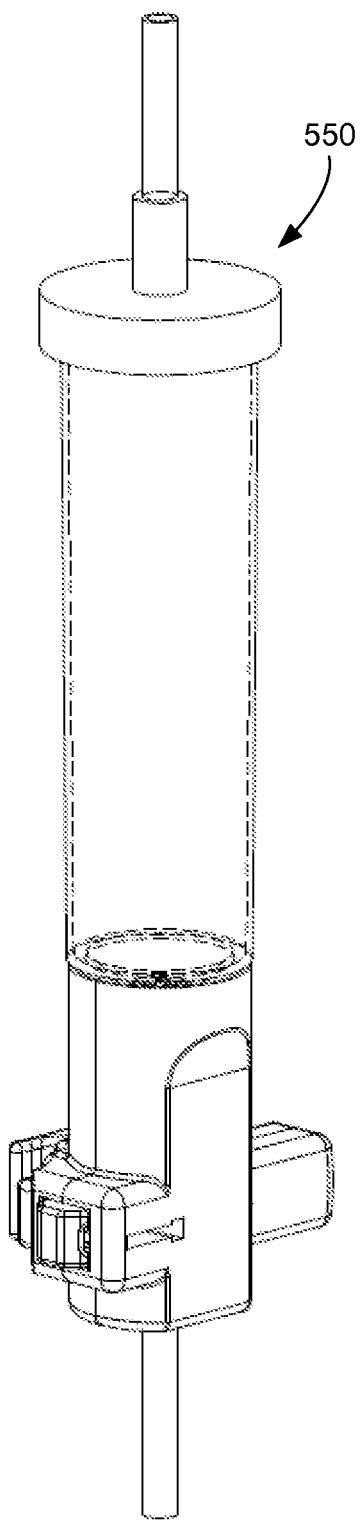
FIG. 7H is a front perspective view of an example of a cartridge.
Figure 7I:
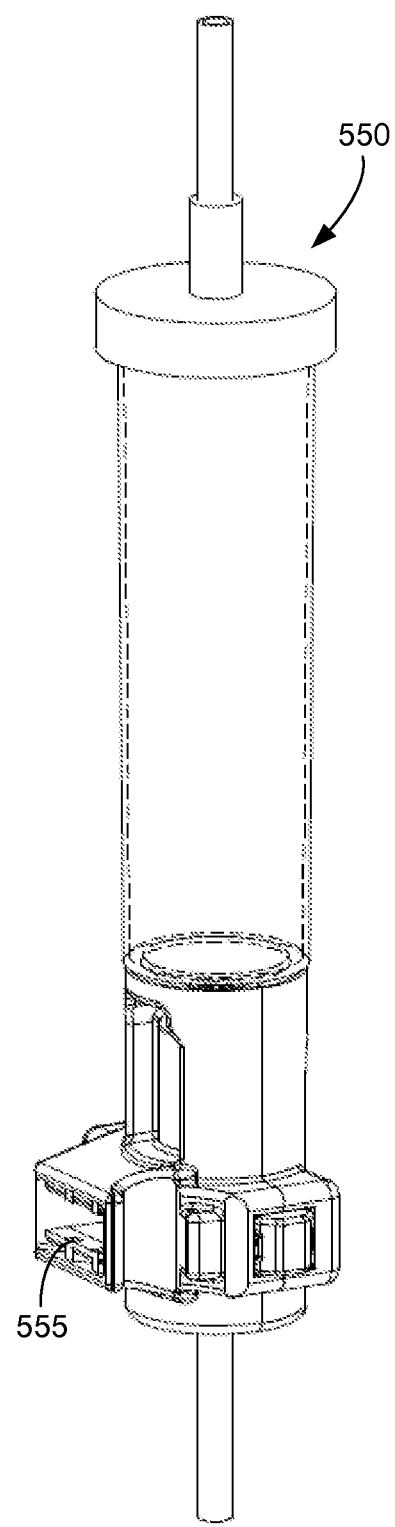
FIG. 7I is a rear perspective view of the cartridge of FIG. 7H.

The ejection and retention mechanism 495 can retain, for example, a cartridge 550 as shown in FIGS. 7H and 7I, which are front and rear perspective views of the cartridge 550. The cartridge 550 includes mounting element 555 that engages with the latch 500 so that the ejection and retention mechanism 495 can retain the cartridge 550 when the latch 500 is in the closed position. The cartridge 550 can include a clamp mechanism, a manual engagement surface, and other features of the cartridge 25 as described with respect to FIGS. 2A and 2B.

Computer System

Figure 8:
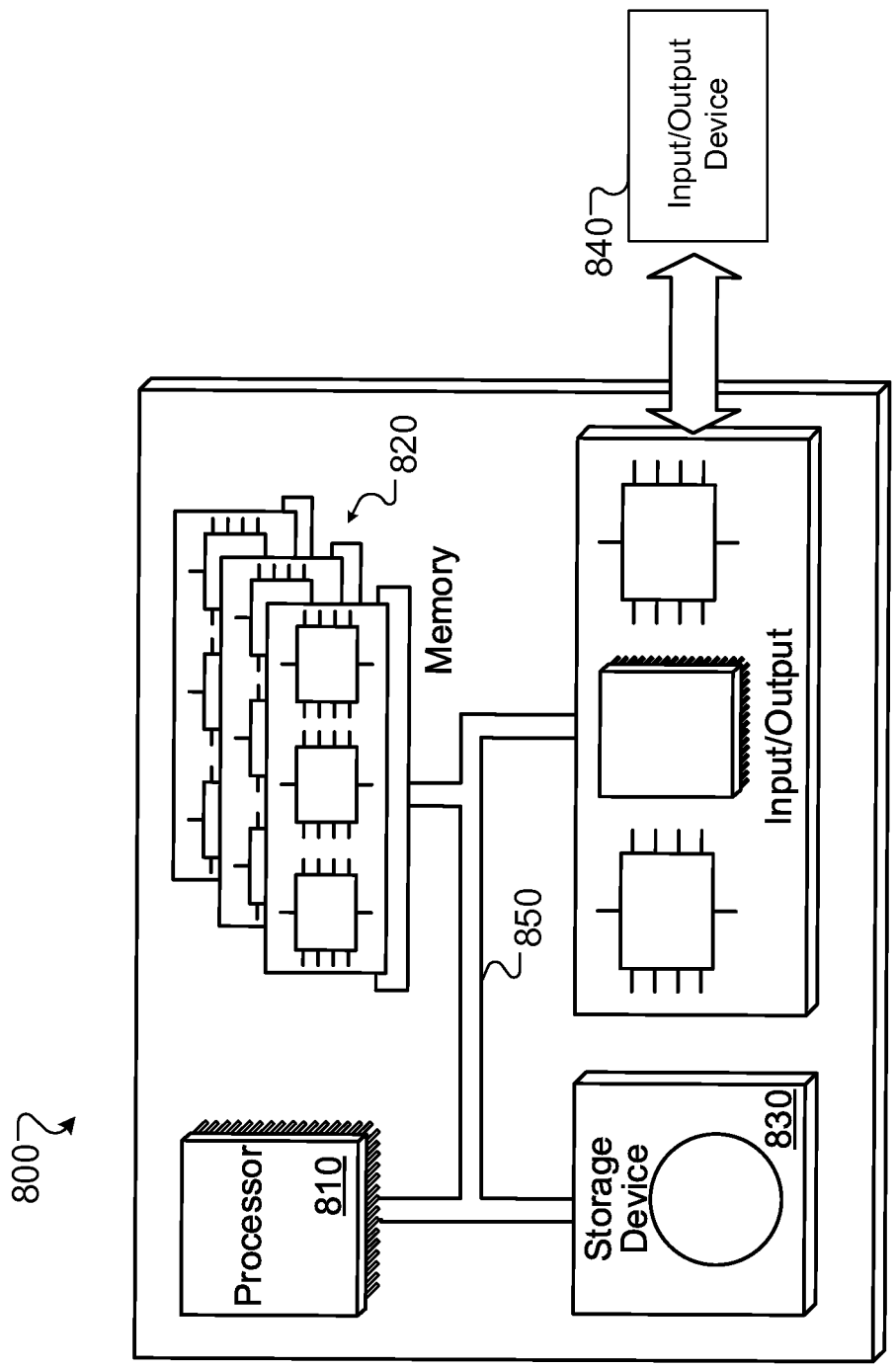
FIG. 8 is a block diagram of a computer system.

FIG. 8 is a schematic diagram of a computer system 800. The system 800 can be used for the operations described in association with any of the computer-implemented methods described herein, according to one implementation. The system 800 can be incorporated in various computing devices such as a desktop computer, a server, and/or a laptop computer. All of or portions of the system 800 can be incorporated into, for example, the external device 215, the central processor 200, the delivery processor 230, the secondary delivery processor 235, and other computing devices described herein. The system 800 includes a processor 810, a memory 820, a storage device 830, and an input/output device 840. Each of the components 810, 820, 830, and 840 are interconnected using a system bus 850.

The processor 810 is capable of processing instructions for execution within the system 800. In one implementation, the processor 810 is a single-threaded processor. In another implementation, the processor 810 is a multi-threaded processor. The processor 810 is capable of processing instructions stored in the memory 820 or on the storage device 830 to display graphical information for a user interface on the input/output device 840. The central processor 200, the delivery processor 230, and the secondary delivery processor 235, for example, can including similar processing capabilities as the processor 810.

The memory 820 stores information within the system 800. In some implementations, the memory 820 is a computer-readable medium. The memory 820 can include volatile memory and/or non-volatile memory. The storage device 830 is capable of providing mass storage for the system 800. In one implementation, the storage device 830 is a computer-readable medium. In various different implementations, the storage device 830 may be a floppy disk device, a hard disk device, an optical disk device, or a tape device. The memory 820 and/or the storage device 830 can store, for example, information pertaining to the treatment of the patient as well as data collected over the course of treatment. The storage device 830 can include parameters that are loaded onto the system 800 or other device of the system 800 to treatment to proceed.

The input/output device 840 provides input/output operations for the system 800. In some implementations, the input/output device 840 includes a keyboard and/or pointing device. In some implementations, the input/output device 840 includes a display unit for displaying graphical user interfaces. In some implementations the input/output device can be configured to accept verbal (e.g., spoken) inputs. For example, the clinician can provide the input by speaking into the input device.

The features described can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 810 carries out instructions related to a computer program. The processor 810 may include hardware such as logic gates, adders, multipliers and counters. The processor 810 may further include a separate arithmetic logic unit (ALU) that performs arithmetic and logical operations.

Methods of Use

FIGS. 7A, 7B, 9, 10, and 11 show an example of how the infusion devices described herein can be used. Before beginning treatment using the infusion devices, the user can prime the patient line and fill the drip chamber 45. The drip chamber 45 and the outlet tube 380 can be primed by gravity using a manual roller clamp to control the rate of gravity flow into the fluid pathway. The user can fill the drip chamber such that a sufficient amount of air is visible to permit visualization of fluid drops as they form.

Figure 9:
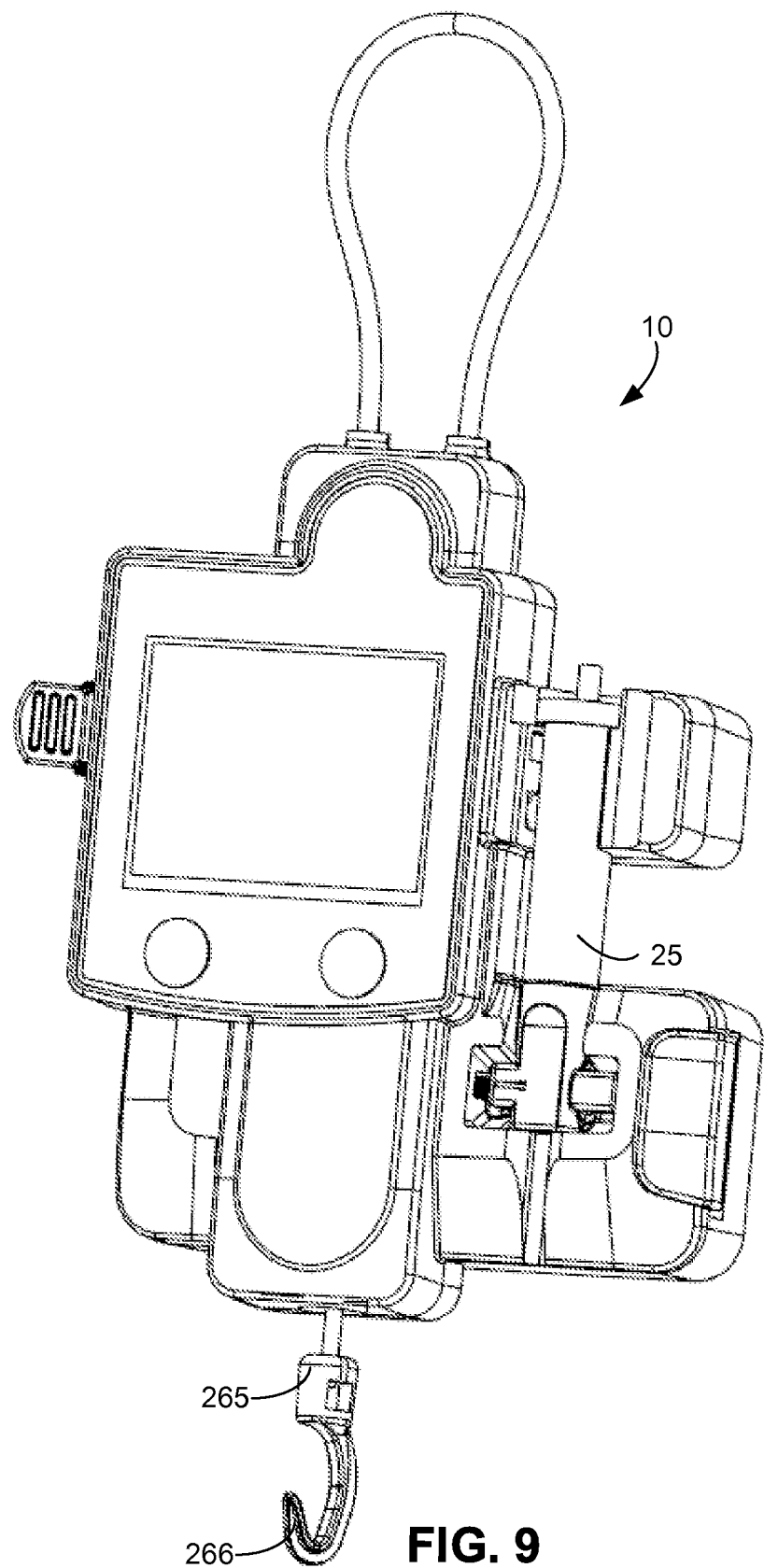
FIG. 9 is a front perspective view of another example of an infuser with a front portion of the infuser removed.
Figure 10:
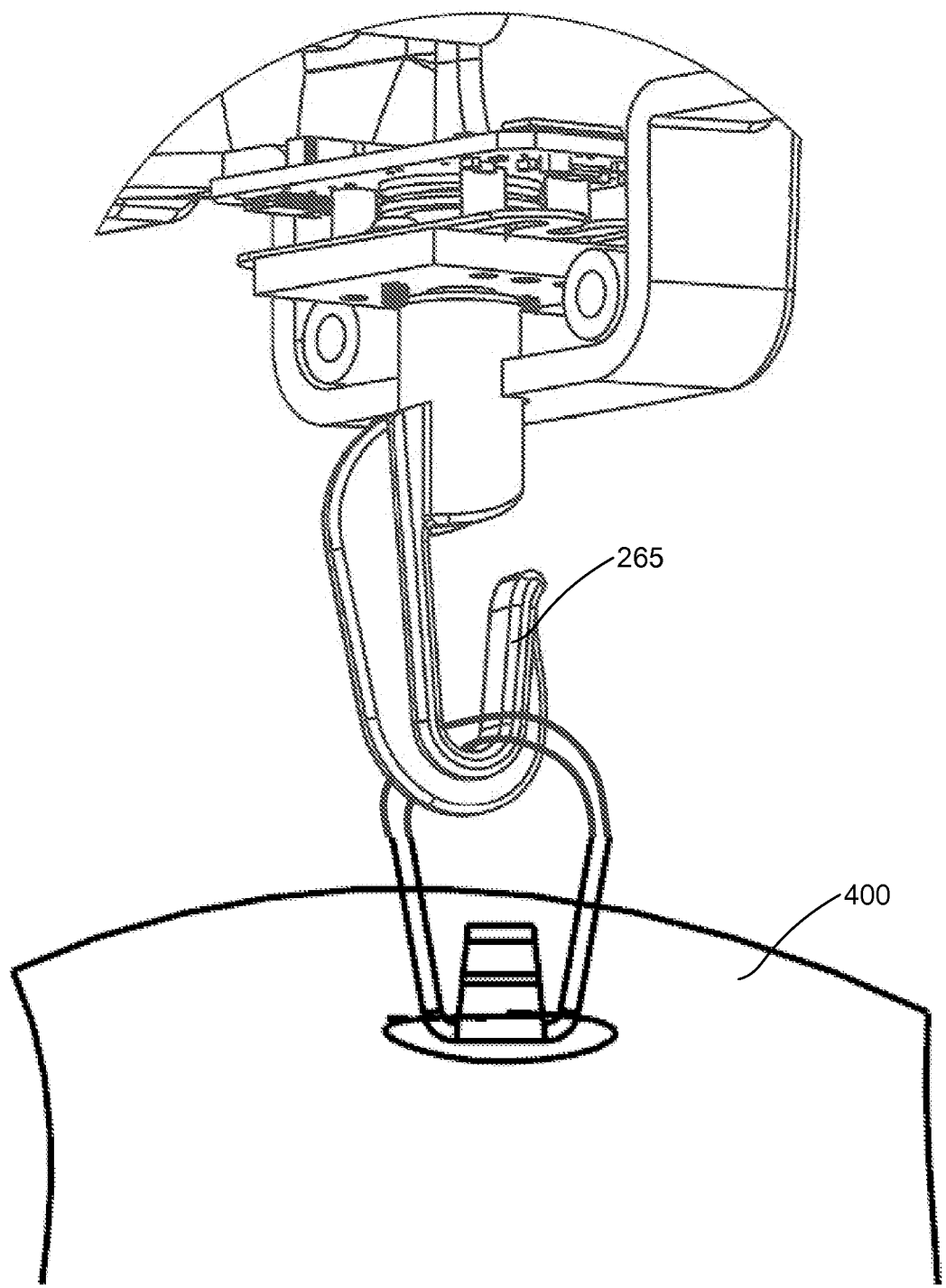
FIG. 10 is a perspective view of an IV container suspended from a load connector of a weight sensor.

As shown in FIG. 9, the load connector 265 of the infuser 10 may include a hook 266 for an IV bag. Referring to FIG. 10, a user, after priming, can hang an IV bag 400 on the hook 266 such that the hook 266, and thereby the weight sensor 30, bears the weight of the IV bag 400. Referring to FIGS. 7A and 7B, a user mounts the cartridge 25, having previously been primed, and containing a desired ratio of air and fluid within the drip chamber, into the cartridge socket 420 of the chassis 15. When the user mounts the cartridge 25, the retention and ejection mechanism can retain the cartridge 25 so that the cartridge 25 is stabilized within the cartridge socket 420 of the chassis 15. The mounting surfaces described herein engage the latch 430 so that the cartridge 25 is securely seated within the chassis 15.

Figure 11:
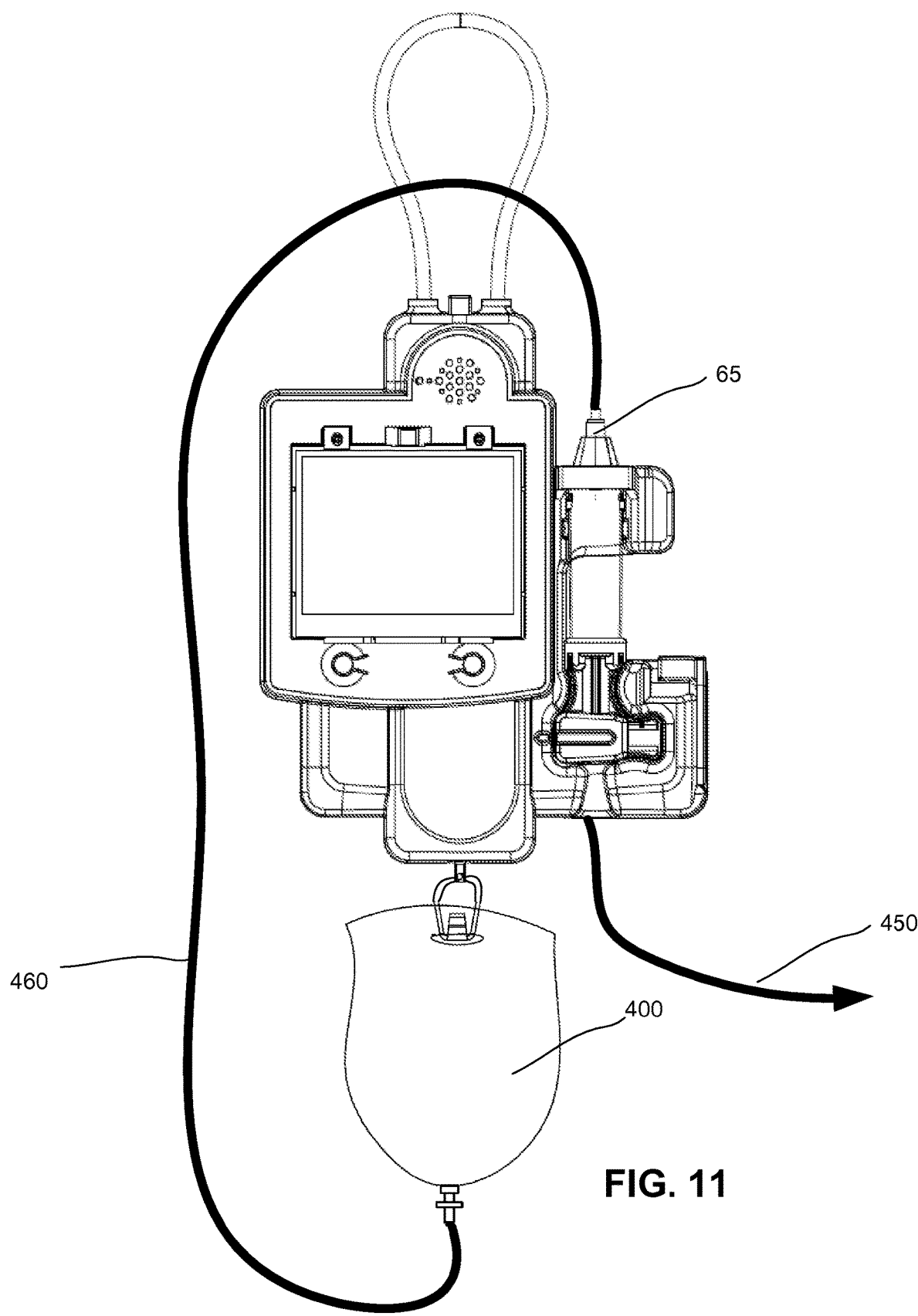
FIG. 11 is a front view of an example of the infuser with an IV container suspended from the load connector, and routing of tubing between the IV container and the cartridge and between the cartridge and the patient.

Referring to FIG. 11, in preparation for treatment, the user can then connect a patient line 450 to the patient and a drip chamber line 460 from the IV bag 400 to the cap 65. The patient line 450 can be connected to or part of the tube 380 extending from the drip chamber 45 and described with respect to FIGS. 6A to 6D. In some implementations, the user can connect the patient line 450 to a flow control mechanism, such as the linear peristaltic pump 600 shown in FIG. 6D. The flow control mechanism can be a clamp mechanism that relies on gravity to drive the flow rate. In some cases, the flow control mechanism can be a pump mechanism, such a linear peristaltic pump. The flow control mechanism can alternatively be a combination of a clamp mechanism and a pump mechanism.

Figure 12A:
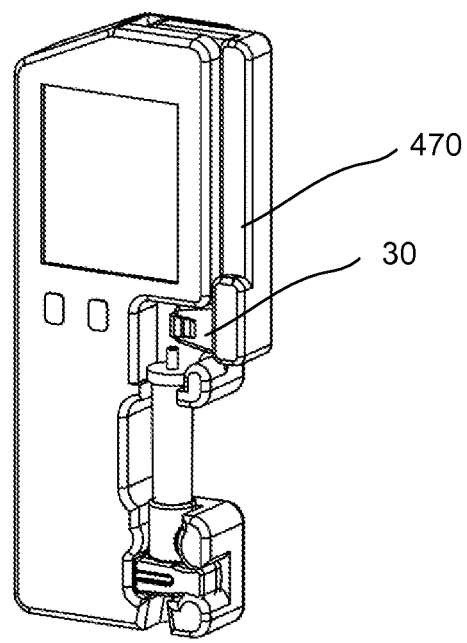
FIG. 12A is a front perspective view of another example of an infuser.
Figure 12B:
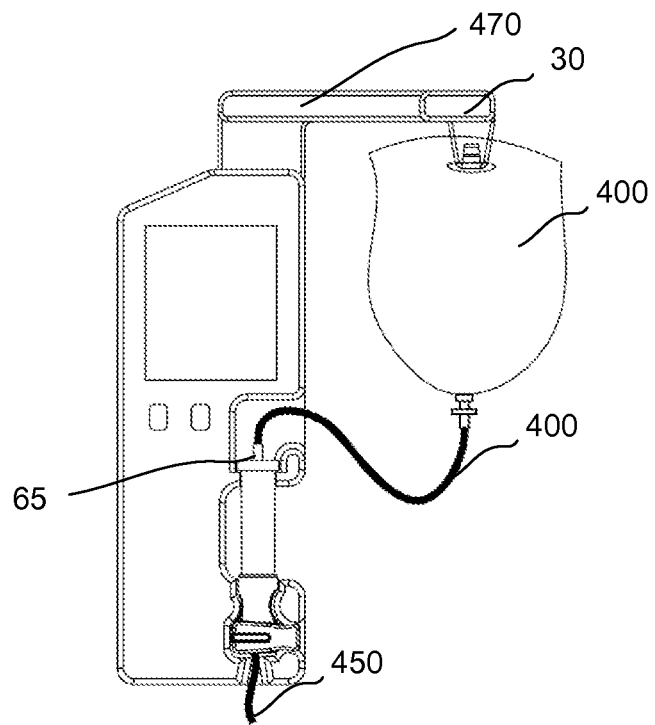
FIG. 12B is a front view of the infuser of FIG. 12A with an attached IV container, cartridge, and tubing.

Now referring to FIGS. 12A and 12B, while the weight sensor 30 has been described to be positioned below the drip chamber, in alternative implementations, the weight sensor 30 can be positioned above drip chamber 45. The load connector 265 and weight sensor 30 can be mounted on a manually retractable arm 470 that stores against the infuser and swings up and locks for use. The patient line 450 connects to the patient and the IV bag 400 connects to the drip chamber 45 via a drip chamber line 460 connected to the cap 65.

In some implementations, the weight sensor 30 and the drop detector 35 can be part of separable modules. Referring to FIGS. 12C and 12D, the weight sensor module 30 can be positioned on a pole extending upwardly from the housing of the drop detector module 35 that receives the drip chamber 45. The weight sensor module 30 can be coupled to a cantilevered hook on which the IV container hangs.

In some examples, the weight sensor module 30 and the drop detector module 35 both hang from a gantry or pole. In some implementations, the weight sensor module 30, the drop detector module 35, the display 20, the flow control mechanism, and/or the volumetric pump are separable and modular components. While the infuser 10 can include the flow control mechanism, the weight sensor 30, and the drop detector 35, in some examples, each of these are separate modules. In some examples, the cartridge 25 includes portions of the flow control mechanism. Alternatively or additionally, a separate flow control mechanism module can include the flow control mechanism and can operate on the tubing 380 extending from the cartridge 25 and/or the patient line 450 to control the flow.

Figure 12E:
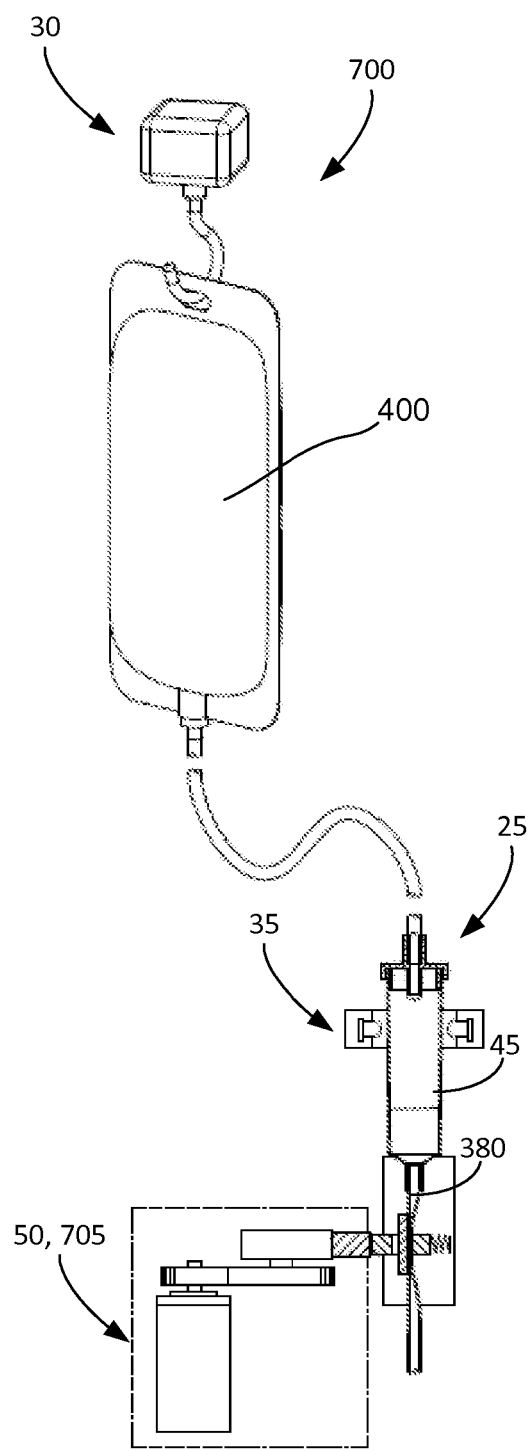
FIG. 12E is a schematic front view of an example of an infusion system.

As shown in an infusion system 700 of FIG. 12E, in further examples, the weight sensor module 30 carries the IV container 400, which in turn is connected to the cartridge 25. The cartridge 25 includes the drop detector module 35. The flow control mechanism is the clamp mechanism 50. The cartridge 25 includes a portion of the clamp mechanism 50, and a flow control mechanism module 705 include another portion of the clamp mechanism 50. The cartridge 25 can include mechanical components, such as a spring or other resilient member that biases the clamp mechanism 50 into the closed position. The flow control mechanism module 705 can include electromechanical or other drive components that control the amount of clamp force generated by the clamp mechanism 50. The flow control mechanism module 705 can include, for example, a motor that drives an arm that interacts with the portion of the clamp mechanism 50 disposed in the cartridge 25. The clamp mechanism 50 can include those features as described with respect to the clamp mechanism 50 of FIGS. 6A to 6C.

The flow control mechanism module 705 can be housed in a chassis (e.g., the chassis 15 of the infuser 10 described herein). The chassis can house the drop detector module 35 and the weight sensor module 30. In some implementations, the flow control mechanism module 705 can be an independent module separate from the drop detector module 35 and the weight sensor module 30. Each of these modules can include a separate housing or chassis as well as independent controllers or processors.

The drop detector module 35, the flow control mechanism module 705, and the weight sensor module 30 can be connected and can cooperate to form the infusion system 700. Each of these modules can interface with fluid carrying components, such as the tubing 380, the drip chamber 45, and the IV container 400 to facilitate control of the flow rate. The modules can each provide signals, as described herein, which can be used by a central processor to estimate the flow rate. The central processor may further be part of a separate computing module that receives the signals and can further transmit control signals to each of the drop detector module 35, the flow control mechanism module 705, and the weight sensor module 30. The modules can also each include a processor independent from the central processor.

In some implementations, each of these modules 30, 35, 705 may include one or more processors electrically connected to wireless transceivers. The wireless transceivers enable communication with a central processor. The modules can communicate with the central processor, which wirelessly transmits control signals to the modules and also receives signals from the modules so that the central processor can, for example, determine the flow rate.

Figure 12F:
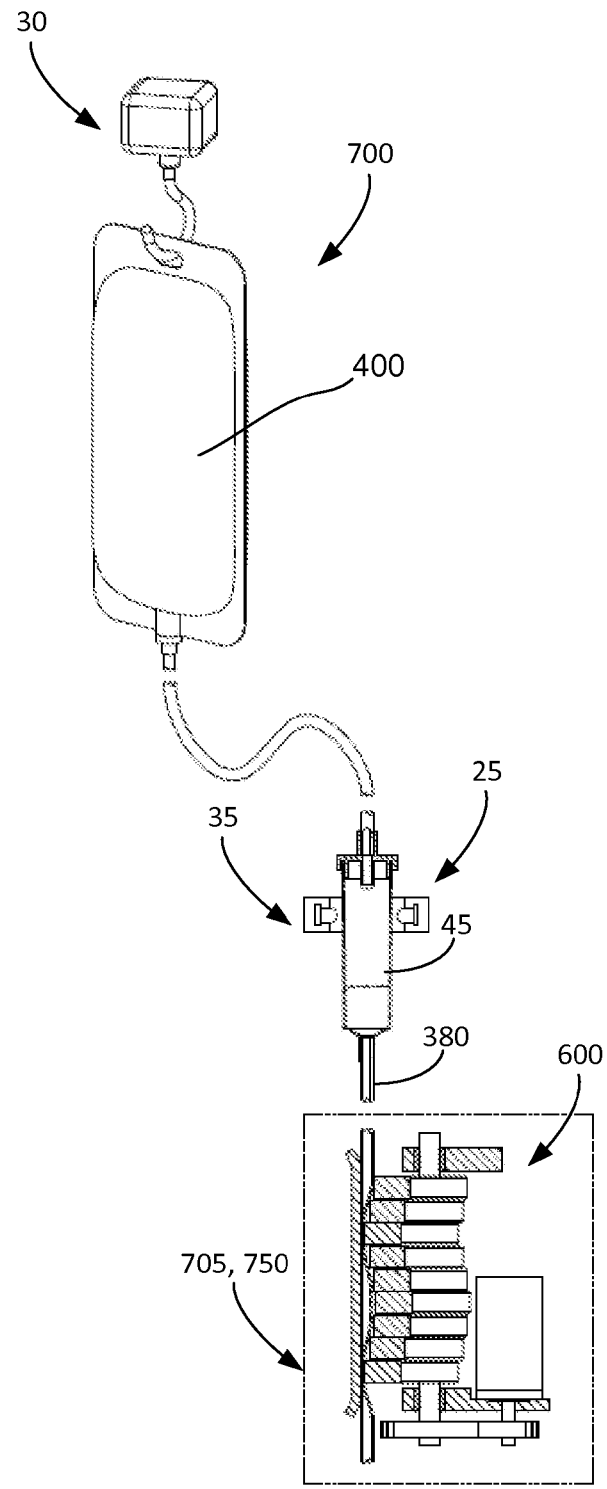
FIG. 12F is a schematic front view of another example of an infusion system.

In some implementations, the flow control mechanism module 705 of the infusion system 700, as depicted in FIG. 12F, can include the linear peristaltic pump 600, which operates on the outlet tubing 380 of the drip chamber 45 to control the flow rate. The flow control mechanism module 705 can thus form a positive displacement pump module 750 independent from the weight sensor module 30 and the drop detector module 35. The pump module 750 includes, for example, the linear peristaltic pump 600, as described with respect to FIG. 6D, and is separate from the drop detector module 35 and the weight sensor module 30. In the example as shown in FIG. 12F, the cartridge 25 does not include a portion of the flow control mechanism, a portion of a clamp mechanism, or a portion of the flow control mechanism module 705. The pump module 750 can receive the outlet tubing 380 or be connected to the outlet tubing 380. In some cases, the pump module 750 can operate directly on the tubing 380. The pump module 750, if configured as a linear peristaltic mechanism, can include a resilient member or platen against which the tubing is compressed by the movement of peristaltic finger elements. In the infusion system 700 depicted in FIG. 12F, the flow control mechanism module 705 can control flow independently from the cartridge 25.

Figure 12G:
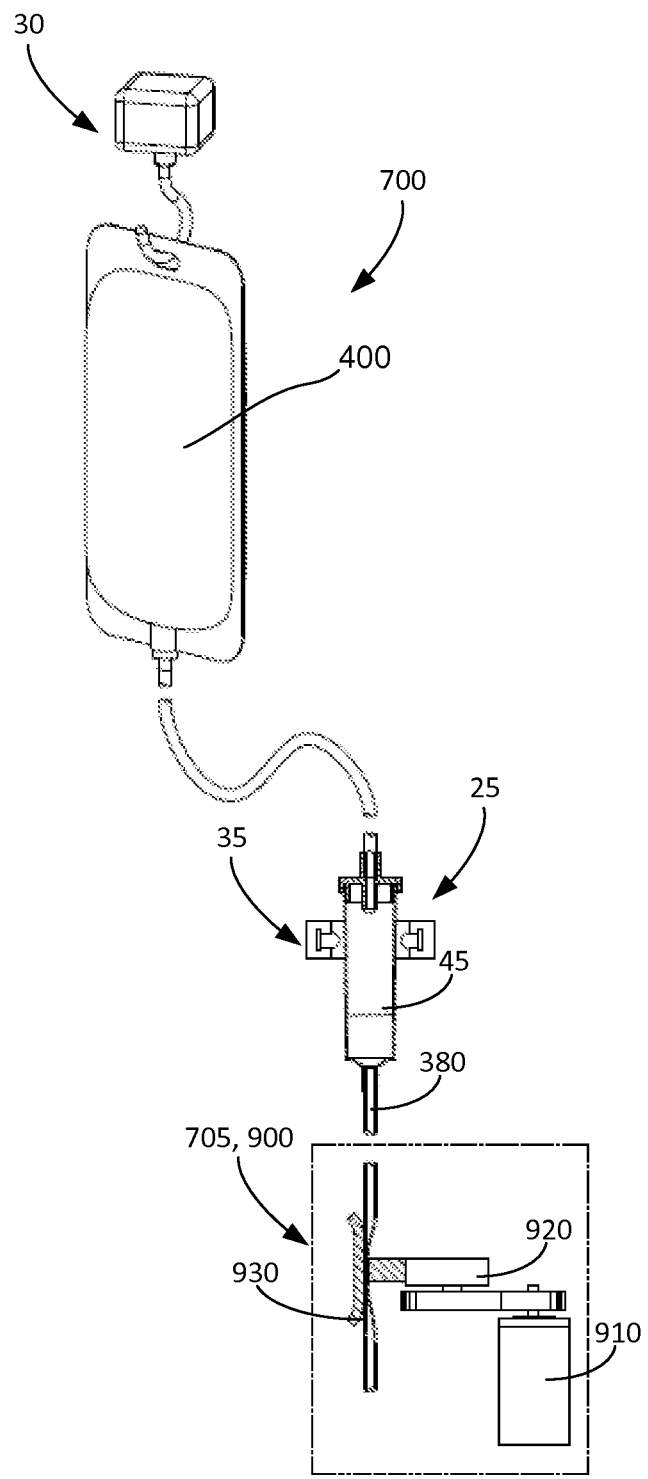
FIG. 12G is a schematic front view of yet another example of an infusion system.

In some implementations, the flow control mechanism module 705 of the infusion system 700, as depicted in FIG. 12G, can be a clamp mechanism module 900 that acts directly on the tubing 380. The clamp mechanism module 900 can include a motor 910 that drives one or more torque and force transfer members to compress the tubing 380. The motor 910 drives the clamping arm 920 toward a resilient member 930. The force of the clamping arm 920 onto the resilient member 930 with the tubing 380 in between the clamping arm 920 and the resilient member 930 can prevent flow through the tubing 380. The resilient member 930 and the clamping arm 920 can be configured such that, without input from the motor 910, the tubing 380 when loaded into the clamp mechanism module 900 is closed. In this regard, the resilient member 930 is loaded to press against the clamping arm 920, thereby causing the tubing 380 to be compressed by default. Alternatively, to protect the tubing conduit from unintended gravity flow during tubing loading or unloading from the clamp mechanism, a device, such as a mechanical interlock, may be included as a secondary tubing occlusion mechanism that is activated when the clamp of the clamp mechanism is open during, for example, loading and unloading of the tubing 380.

The clamp mechanism module 900 functions as a pinch valve and can include features similar to those described with respect to the clamp mechanism 50. In the example as shown in FIG. 12G, the cartridge 25 does not include a portion of the clamp mechanism. Rather, the tubing 380 of the cartridge 25 can be loaded or connected to tubing loaded into the clamp mechanism module 900 such the clamp mechanism module 900 can control the flow rate of the fluid from the drip chamber 45.

Combinations of the clamp mechanism 50, the pump module 750, and the clamp mechanism module 900 can be implemented into the infusion system 700. For example, the infusion system 700 can include both the pump module 750 and the clamp mechanism module 900. The pump module 750 can be used to pump fluid to the patient at a desired flow rate, and the clamp mechanism module 900 can be used a safety shut-off valve or as an alternate flow control mechanism. The infusion system 700 can also include both the clamp mechanism 50 and the clamp mechanism module 900, where the clamp mechanism 50 can control the flow rate and the clamp mechanism module 900 can be used for a safety shut-off in case the clamp mechanism 50 fails.

Furthermore, the cartridge 25 can include the drop detector module 35 as well as portions of the flow control mechanism 705. In some implementations, the cartridge 25 and the drop detector module 35 are also separable.

Figure 13:
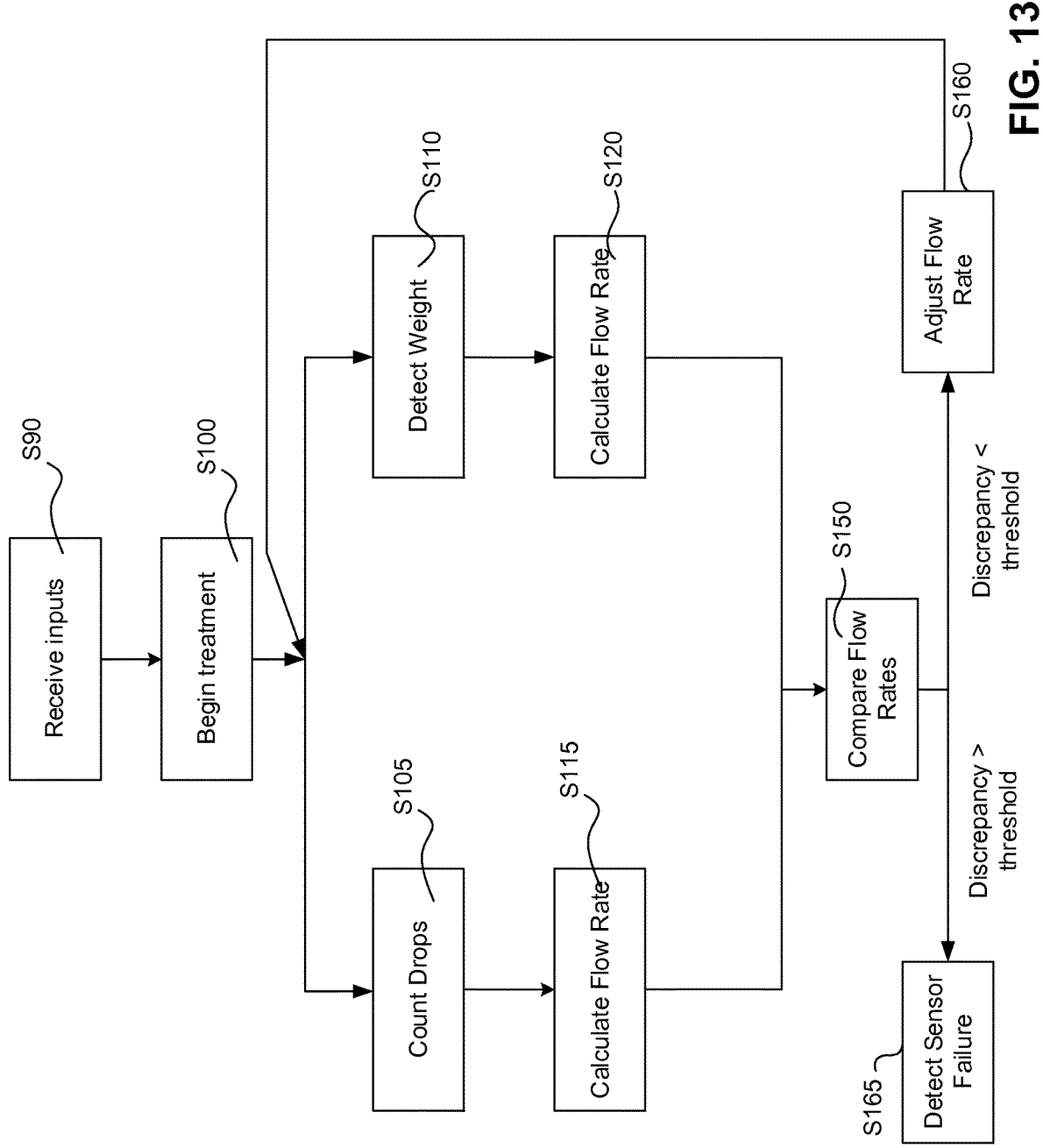
FIG. 13 is a flow chart of an example of a flow control process implemented by a central processor shown in FIG. 3.

FIG. 13 shows a flow chart of an example process for controlling flow rate during treatment. One or more processors of the infuser can implement a drop count-based and weight-based flow rate determination process. Referring to FIG. 3 and FIG. 11, at step S90, the central processor 200 receives inputs pertaining to the treatment. The inputs can include, for example, information on fluid parameters, flow control mechanism parameters, and cartridge configurations. The inputs received at step S90 can be user-defined inputs. For example, the user can pre-define the medical fluid to be delivered by selecting from one of the medical fluids in the medical fluid library. In some cases, the user can specify a specific gravity and a viscosity of the medical fluid to be delivered. In some implementations, the user can select the flow control mechanism and can indicate a size of the drip chamber and tubing used for the infuser.

Fluid parameters used in the flow determination process can include, for example, specific gravity, viscosity, opacity, surface tension, empirically derived information about drop size as a function of drop forming element size and fluid flow rate, and other information relevant to fluid delivery. The fluid parameters may be stored in a medical fluid library that includes a database of medical fluids and their fluid parameters. The medical fluids can include drug solutions, infusion solutions, and other medical fluids that may be delivered to a patient during treatment.

Flow control mechanism parameters used in the flow determination process can depend on the type of flow control mechanism used by the infuser. As described with respect to FIGS. 6A to 6D, the flow control mechanism can be, for example, a clamp mechanism or a positive displacement pump. The cartridge configurations can include a drip chamber and drop forming element size, tubing size, and other parameters that can influence flow rate from the cartridge.

The inputs can also include information identifying an operation mode, such as a treatment mode or a testing mode. In the treatment mode, the central processor 200 can control the flow control mechanism and the sensors of the infuser to deliver a desired amount of fluid to the patient. The treatment mode can further include other pre-defined modes of therapy, such as, for example, time varying infusions, a sequence of flow rates at defined future times, infusions responsive to measurement of a physiological parameter of a patient, administration of secondary medications, and configurations permitting remote control of the device by an external device.

In addition to or as an alternative to receiving inputs defined by the user, the central processor 200 can receive self-determined or default inputs. For example, in some implementations, the self-determined inputs may include predetermined default configurations stored in the medical fluid library. In the testing mode, the central processor 200 can test operations of the infuser to ensure that the flow control mechanism and the sensors are functioning properly. In some cases, in the testing mode, instead of relying on a user input of the treatment parameters, the central processor 200 controls the flow control mechanism and monitors the sensors to determine those parameters. For example, the user can pre-define the viscosity and the specific gravity of the medical fluid to be used during the testing mode. The central processor 200 can then determine the flow control mechanism parameters by detecting the volume of fluid delivered using the weight sensor 30 and the drop detector 35. The central processor 200 can compute a flow rate and, based on the flow rate, define the flow control mechanism parameters. In some cases, the user defines the flow control mechanism parameters, and the central processor 200 determines the viscosity and specific gravity of the medical fluid to be delivered. Other inputs may include a size, dimension, and geometry of the drop-forming element in the cartridge, a desired amount of fluid delivery, a duration of delivery, and/or a type of medical fluid to be delivered to the patient. The inputs may further include an indication of whether this operation corresponds to a first initiation of fluid flow, or an adjustment to an already-flowing infusion.

At step S100, the central processor 200 can receive a user input to initiate treatment. The user input can be provided, for example, using a user interface, or one or more input/output devices such as the external device 215, the display 20, or the keypad 210. Upon receiving the indication to begin treatment at step S100, the central processor 200 begins the treatment. At the beginning of the treatment, the central processor 200 can activate the flow control mechanism and begin delivering fluid at a default rate, which may be different than the desired flow rate. The central processor 200 also initiates the sensors of the infuser, including the weight sensor 30 and the drop detector 35. In some cases, the sensors and the flow control mechanism can already be active, as they were previously operated during the testing mode of the central processor 200.

During operation, during steps S105 and S110, the central processor 200 regularly monitors and controls the optical drop detector 35 and weight sensor 30. The infuser has at least these two independent devices to monitor a flow rate of the fluid flow.

During steps S105 and S115, the drop detector 35 can provide both a short-term and long-term measurement of fluid movement through the tube set. Using the drop detector 35, at step S105, the central processor 200 counts the number of drops. The central processor 200 uses medical fluid library information to determine a predicted drop size for a given medical fluid, with any necessary scaling factors to adjust predicted drop size as a function of flow rate. The central processor 200 can estimate the flow rate at step S115 based on the number of drops counted during a certain period of time. The estimate can be based on the volume of the drop—as determined based on, for example, the viscosity and specific gravity of the medical fluid—the number of drops counted, the dimensions of the drop forming nozzle element of the drip chamber, and the period of time in which those drops were counted. To improve the accuracy of the estimate, the central processor 200 can compute the flow rate over larger periods of time with several drop events.

With regards to the short-term measurement, upon counting a certain number of drops over a time period during step S105, the central processor 200 can use the expected volume of the drop size of the medical fluid to calculate the fluid flow rate during that time period during step S115. The period of time over which the central processor 200 uses the signals from the drop detector 35 to determine the flow rate for the short-term measurement is, for example, between 1 second and 5 seconds, 5 seconds and 15 seconds, or 15 seconds and 30 seconds. In some cases, for slower flow rates, the short-term measurement occurs over longer intervals. The short-term measurement can also be selected based on a number of drops that occur during the interval. For example, the duration of time can be the amount of time required for a certain number of drops to fall. The number of drops can be between 10 and 20 drops, 20 and 30 drops, and 30 and 40 drops. The flow rate may also vary depending on the size of the drop forming element, which can be configured for flow rates between, for example, for example, 10 drops/ml, rather than 60 drops/ml.

In some implementations, to further improve the estimate, the central processor can correct or adjust the estimate by removing artifact data generated by the drop detector 35. For example, the central processor 200 can determine if the drop detector 35 failed to detect a drop due to a missing drop or a double drop event. The central processor 200 can estimate the flow rate based on detecting two drops in a period of time and compare the flow rate in that period of time to the estimated flow rate of a previous period of time of equal duration. If the central processor 200 detects a discrepancy between the flow rates to satisfy a threshold condition, e.g., between 190% to 210% difference between the flow rates, the central processor 200 determines that a missing drop event (if the present flow rate is less) or a double drop event occurred (if the previous flow rate is less). If the present flow rate is less than the previous flow rate, a missing drop event is determined to have occurred. The central processor 200 can correct the average flow rate computed over a large interval by modifying the data to account for a drop, even though the drop detector 35 does not detect the missing drop. If the present flow rate is greater than the previous flow rate, a double drop event is determined to have occurred. In such a case, the central processor 200 can correct the average flow rate computed over a large interval by modifying the data to indicate that only one drop occurred even though the drop detector 35 detected two drops.

The central processor 200 can also adaptively modify the period of time over which the central processor 200 uses the drops detected by the drop detector to determine the flow rate. For example, if the central processor 200 is not adjusting the flow rate of the flow control mechanism, the central processor 200 can increase the size of the period of time to, for example, 30 seconds to 1 minute, 1 minutes to 5 minutes, or 5 minutes to 10 minutes. The central processor 200, in some cases, increases the number of drops used to determine the flow rate. For example, the period of time can correspond to period when a certain number of drops have fallen. The number of drops can be between 30 and 60 drops, 60 and 100 drops, or 100 and 200 drops.

During steps S110 and S120, the weight sensor 30 provides a long term measurement of flow rate based on the change in fluid weight in the IV container and the density of the medical fluid being delivered. First, during step S110, the weight sensor 30 detects a fluid weight in the IV container and generates a signal indicative of the weight and received by the central processor 200. Based on the density data or specific gravity data of the medical fluid that the central processor 200 received at step S90, the central processor 200, during step S120, can calculate the flow rate based on weight changes over time. The estimation of flow rate using weight sensor 30 may operate in different modes, depending upon whether an infusion treatment is being initiated for the first time, is in a lengthy steady state, or is subject to an adjustment or initiation of a fluid bolus of fluid at a substantially different rate for a period of time.

At step S150, the central processor 200 can compare the flow rates calculated at steps S115 and S120. The central processor 200 measures a discrepancy between the estimated flow rates. The central processor 200 may determine that the discrepancy is below or above an acceptable threshold. The threshold can be a percent difference between the estimated flow rates. The threshold can be between, for example, 0.1% and 1% or 1% and 5%. The threshold can be a user defined input received at step S90. In some implementations, the threshold may be selected by the central processor 200 based on the medical fluid being delivered. For example, if the medical fluid contains a drug that must be delivered at very accurate doses, the threshold may be lower. A table of such particular thresholds for particular medical fluids or drugs, may be stored in the medical fluid library.

If the discrepancy is below the acceptable threshold, at step S160, the central processor 200 continues the treatment. If the central processor 200 determines that the flow rate is below or above the desired flow rate set at the beginning of treatment, the central processor can adjust the flow control mechanism so that the flow rate approaches the desired flow rate. In some cases, if the estimated flow rate is within a predetermined interval about the desired flow rate, the central processor 200 maintains the flow rate at the controlled value. The predetermined interval can be, for example, 95% to 105%, 99% to 101%, 99.5% to 100.5%, or 99.9% to 100.1% of the desired flow rate.

The combination of the outputs from the two sensors can be used for real-time error correction (or near real-time error correction) for flow control at step S160. For example, if the weight sensor 30 and drop detector 35 both detect a flow rate less than the desired flow rate, the processor, at step S160, can actuate the flow control mechanism so as to increase the flow rate to a desired level. The central processor 200 can also cross-reference flow rate computed using the drop detector 35 at step S115 with the data computed using the weight sensor 30 at S120 to reject a missing drop event, a double drop count event, or erroneous drop detections due to drop splashing or drops on walls of the drip chamber.

In some cases, the central processor can periodically send control signals to the flow control mechanism regardless of whether the flow control mechanism is to be adjusted to change the flow rate. The central processor can adjust the periodically transmitted control signal when the flow rate is to be changed. In some implementations, the processor only sends control signals to the flow control mechanism when the flow rate is to be changed. The flow control mechanism can include a delivery processor that receives the control signals from the central processor. The delivery processor in turn can transmit instructions to the flow control mechanism to adjust, maintain, or shut off the flow rate.

In some cases, the central processor 200 determines the flow rate at step S160 by taking a weighted average of the flow rates determined using the data from the weight sensor 30 and the drop detector 35. The weighted average can depend on the fluid parameters of the medical fluid being delivered. The specific gravity and viscosity of the medical fluid can indicate that one of the drop detector 35 and the weight sensor 30 will more accurately predict the flow rate, and thus, the central processor 200 may provide greater weight to the estimation determined using data from that sensor. In some implementations, the central processor 200 adjusts the flow rate based on the flow rate determined by the data from one of the drop detector 35 and the weight sensor 30 and uses the other data for error correction.

In some implementations, at step S160, the central processor 200 can analyze a time series of data from the weight sensor 30 and the drop detector 35. The central processor 200 can determine that the flow rate determined at step S115 using the drop counter is consistently below the flow rate determined at step S120 using the weight sensor 30. The central processor 200 can conclude that the drop detector 35 is not functioning properly and proceed to determine flow rate using only the weight sensor 30. The central processor 200 thus determines a sensor failure has occurred.

In implementations where the flow control mechanism is the clamp mechanism or other non-deterministic system as described with respect to FIGS. 6A to 6C, after adjusting the flow rate at step S160, the central processor 200 can verify that the flow rate has changed after actuating the clamp mechanism by estimating the flow rate using the drop detector and the weight sensor. The control process can be configured such that the clamp mechanism 50 does not move to a position that results in flow much above the desired rate. If the current flow is less than the desired flow, the clamping force is reduced in small increments and the flow rate is checked using the drop detector 35 and the weight sensor 30 before advancing further. Over time the flow rate will tend to decrease rather than increase since the head pressure produced by fluid in the IV bag will gradually drop and the tubing will tend to relax to a more compressed state due to strain relaxation.

In implementations where the flow control mechanism is a deterministic system such as the linear peristaltic pump described in FIG. 6D, after the flow rate has been adjusted at step S160, the central processor 200 can compare the flow rate measured by the weight sensor 30 and the drop detector 35 with the expected flow rate of the linear peristaltic pump based on motor revolutions to confirm that the adjusted flow rate matches the estimated flow rates after adjustment. In some cases, the adjustment to the flow control mechanism may be an iterative and recursive process in which the central processor 200 makes multiple adjustments with intervening flow rate checks using the data from the weight sensor 30 and the drop detector 35 to reach the desired flow rate.

As described herein, in some examples, the infuser uses a pump. In particular, the pump can be a positive displacement pump. In this regard, the central processor 200 can estimate the flow rate of the fluid based on the duty cycle of the pump. This estimated flow rate provides another degree of orthogonality for the central processor and infuser. To improve the accuracy of the estimated delivery flow rate, the central processor 200 can further compare flow rates determined by each of the drop counter and the weight sensor 30 to flow rate estimated using the parameters of the positive displacement pump. The central processor 200 can perform statistical analysis on a time series of each of the three orthogonal estimations of flow rate. In some cases, after comparing these flow rates, the central processor 200 can simply determine that the estimated flow rates sufficiently correspond to one another, e.g., the estimate flow rates are all within the acceptable threshold. Thus, at step S160, the central processor 200 can compute an aggregated flow rate based on all of these estimations and adjust the flow rate based on the aggregated flow rate. The aggregated flow rate can be a weighted average of these estimations. In some examples, the aggregated flow rate is one of the estimations, and the remaining estimations are used to correct artifact data.

In some implementations, to correct artifact data, the central processor 200 can receive signals from other sensors connected to the drop detector 35, the weight sensor 30, and/or the infuser. For example, an accelerometer, such as the accelerometer 212, can detect motion of the infuser. Based on signals from the accelerometer 212, the central processor 200 can determine that the infuser has experienced an anomalous force or acceleration reading during a period of time. The central processor 200 can check the data collected from the weight sensor 30 and/or the drop detector 35 during that period of time to determine if the data collected also shows anomalies. The central processor 200 can filter out the data collected during this time period by excluding the data from the computed aggregated flow rate. In some examples, the central processor 200 can further receive signals from other types of sensors to account for artifact data. The sensors can include ambient light detectors, motion sensors, such as acoustic sensors or optical sensors that detect motion of the drop detector 35, the weight sensor 30, and/or the infuser, or which detect ambient light conditions detrimental to proper operation of the drop detector.

The central processor 200 can determine which of the estimates is the flow rate used to make adjustments to the flow rate toward the desired flow rate based on the inputs received at step S90. For example, if the pump is a reciprocating piston pump with a rapid refill stroke, fluid entering the drip chamber may enter as a flow as opposed to a countable drop. If the central processor 200 receives the input at step S90 indicating the flow control mechanism is a reciprocating piston pump with an intermittent rapid refill stroke, the central processor 200 can perform estimations of the flow rate without using the drop detector 35, as the data from the drop detector 35 is likely more inaccurate than the flow rate determined by the weight sensor 30 or the pump speed.

After the central processor 200 adjusts the flow rate at step S160, the central processor 200 can continue treatment and continue monitoring the flow rate of the treatment. The central processor 200 can continue performing steps S105, S110, S115, S120, S150, and S160 until the treatment is complete or until the central processor 200 detects a discrepancy in the flow rate estimates greater than the threshold.

At step S150, the central processor 200 may compare the flow rates and determine that a discrepancy larger than the threshold has occurred. In such a case, at step S165, the central processor can detect a failure of either monitoring system 30, 35. Therefore, the central processor, by monitoring both the weight sensor 30 the drop detector 35, adds orthogonal redundancy to the operation of the infuser. In some implementations, detecting a failure may result in automatic ejection of the cartridge or immediate clamping of the tube set. For example, the central processor can activate the clamp mechanism or activate the ejector motor to actuate the ejection mechanism.

In some cases, at step S150 and S165, the central processor 200 can determine that consecutive failures of, for example, the drop detector, and interpret the consecutive failures as a change in flow rate. For example, if the time interval between drops decreased consistently for two or more consecutive drops, the central processor may conclude that the fluid flow rate increased. As described above, if the central processor determines a change in flow rate based on the drop detector, the flow rate change can be verified by calculating the flow rate based on the weight sensor 30.

At step S165, the central processor 200 may detect a sufficiently large discrepancy between the flow rates. In particular, the central processor 200 may determine that one of the several estimated flow rates (e.g., the pump-based estimation, the drop detector-based estimation, and/or the weight sensor-based estimation) is inconsistent with the others. The central processor 200 can proceed with treatment without considering the inconsistent estimated flow rate in estimating the aggregated flow rate. Thus, the central processor 200 can implement a process capable of safe continued operation of the device, while ignoring one or more of the flow rate determined by the positive displacement pump, the flow rate determined using the drop detector, or the flow rate determined using the weight sensor 30.

In some implementations, the estimations of the flow rate using the drop detector 35 and the weight sensor 30 can compensate for inaccuracies with the fixed volume delivered by the positive displacement pump from cycle to cycle. For example, due to inelastic deformation of tubing used for the positive displacement pump, the volume delivered by the positive displacement pump in a single cycle may change over time. The central processor 200, using the signals received from the drop detector 35 and the weight sensor 30, can detect the increasing inaccuracies by determining that the flow rate as measured by the peristaltic pump is inconsistent with the flow rates measured by the drop detector 35 and the weight sensor 30. The central processor 200 can determine that the flow rate estimated using the peristaltic pump is no longer sufficiently accurate and can update the estimate of the fixed volume per cycle being used in the process for aggregate flow rate. Alternatively, the central processor can ignore the flow rate calculated from the action of the peristaltic pump. The central processor 200 can compute the flow rate based on the signal received from the drop detector 35 and the weight sensor 30 alone.

At step S165, in response to detecting the large discrepancy, the central processor 200 can issue different alerts depending on the estimated flow rates. For example, the central processor can issue a "stop" alert, a "maintain" alert, or a "warning" alert. The central processor 200 issues the "stop" alert to stop the treatment or indicate that the treatment should be stopped. The alert can cause the cartridge socket 420 to eject the cartridge 25 to stop the treatment or can cause the flow control mechanism to stop delivering fluid. The central processor issues the "maintain" alert if the central processor 200 determines that the large discrepancy was, for example, caused by artifact or unreliable data. The central processor 200 issues the "warning" alert if the central processor 200 has determined that further monitoring of the treatment will ignore one of the flow rates due to inaccuracies. The "warning" alert can indicate to the user that, although the treatment need not be stopped, the flow rate is only being measured by less than all of the several systems available to measure the flow rate (e.g., the drop detector, the weight sensor, and/or the positive displacement pump).

The central processor 200 further includes a control process that interprets information from the drop detector 35 and the weight sensor 30. For example, the control process can produce a different logic signal when the drop detector 35 has detected a drop. To detect a drop, an exemplary implementation may measure the duration of high pulses emitted by the IR detector. For example, when the infuser is idle, the IR detector can generate periodic 2 millisecond high pulses, which correspond with 2 millisecond "off" periods of the IR LED. These pulses generate interrupts to the central processor 200, which measures the width of the output pulse. The central processor 200 is programmed to recognize a drop event, which can be defined as receiving a pulse width of greater than a certain duration that may vary depending on the medical fluid delivered. In some implementations, a higher viscosity medical fluid can result in a larger drop size and therefore a higher expected pulse width. This duration can be as low as 4 milliseconds. In such an implementation, if the width exceeds 4 milliseconds, the controller interprets this as a drop event and sends, for example, an 8 milliseconds actuation pulse to signal to the delivery processor 230 to actuate the clamp mechanism 50, which thereby controls the flow rate. The central processor 200 may also send logic signals based on the number of pulses detected. For example, in some implementations, the IR detector can generate a logic "low" on its output after detecting a nominal number of pulses, e.g., 6 pulses, of a 38 kHz pulse train. If a train of 6 pulses is not detected, the detector generates a logic "high" on its output. In response to the logic high, the central processor 200 may then send a control signal to the clamping mechanism 50 to deliver fluid to the patient.

In one exemplary use of the drop detector of the infuser, power reduction methods can be used to reduce the amount of power delivered to the IR LED. For example, the pulse train driving the IR LED can be "chopped" to produce a 1 millisecond burst of pulsed light (38 pulses @ 38 kHz) followed by 2 milliseconds of quiescence, repeating indefinitely during normal operation.

To ensure that the drop detector 35 is functioning properly, the central processor 200 can send calibration instructions to determine that the detector 35 is working. In one example of calibration, when the central processor 200 initializes the system, the central processor can perform a calibration of the drop detector 35 as follows. The duty cycle of the IR LED pulse train is dropped to a very small percentage, e.g., close to zero, at which point no pulses are visible to the IR detector. The pulse train is chopped to yield one-millisecond light pulses followed by one millisecond of darkness, repeating this pattern three times. If the output of the IR LED has adequate illumination for the IR detector to sense the IR light, the detector will generate three logic "lows", which are counted as events by the controller. If three events are not detected, the duty cycle (i.e., effective emitter power) is increased slightly and another calibration cycle is run. If the three pulses are detected, the test can be run at the same power level twice more to confirm the reliability of the setting. While the infuser is in operation, periodic re-calibrations are performed, such as immediately following the detection of a drop.

Under normal conditions the flow can be shut off using the flow control mechanism described above. For example, the central processor can activate the clamp mechanism to stop the fluid flow, or the central processor can stop the positive displacement pump to prevent flow past the pump. The user may also manually dismount the cartridge by depressing the cartridge ejector 34 using the mechanisms described with respect to FIGS. 7A to 7I or by simply pulling out the cartridge from the cartridge socket.

In some implementations, the infuser may include an additional, independent mechanism that can respond to certain conditions, such as fault conditions, to automatically stop the flow by ejecting the cartridge from the chassis. This safety mechanism can have an independent power supply, controller, and actuator. Its controller monitors the main power supply and main controller and acts to eject the cartridge in case of the detection of an electronic, power, mechanical, or software failure of the main flow control mechanism. The independent mechanism can be the clamp mechanism, and the flow control mechanism can be the positive displacement pump. In some cases, the central processor 200 can issue the "stop" alert and cause the ejector motor to actuate to cause ejection of the cartridge from the cartridge socket.

In cases where the cartridge uses the clamp mechanism to control flow, if the cartridge is ejected or pulled from the infuser, the movable clamp element, which is biased to the closed position by spring 370, will immediately act to cut off the flow through the tube. In cases where the cartridge uses the positive displacement pump to control the flow, the positive displacement pump will immediately shut off to prevent any further fluid delivery.

EXAMPLES

The infusers described above are further illustrated in the following examples, which do not limit the scope of the claims.

Example 1—Calculating Drop Size Based on Weight

An example of an algorithm to calculate drop size based on weight was verified experimentally.

Methodology

The infuser used in this experiment was designed to operate with a 20 drop per milliliter (ml) drip chamber, thus each drop had an expected volume of 0.05 ml. In actual use, the actual drop volume will differ from the expected volume. The infuser further included the weight sensor that regularly monitored the weight of the IV container that delivered medical fluid. The algorithm implemented in this experiment assumed the specific gravity of the infusate to be that of water, 0.9982 grams/mL, though it should be understood that in other examples, the specific gravity can be customized for the medical fluid being delivered.

At the beginning of the infusion, there was no weight data from which to derive a weight—and subsequently volume—per drop. The control algorithm used the expected drop volume until the volume of fluid dispensed was sufficient to compute a drop volume. Once this volume, about 1.25 mL, was accumulated, the algorithm then computed a drop weight by dividing the total weight of fluid infused by the total number of drops detected. Using this weight per drop, a drop volume was computed by dividing the drop weight by the fluid's specific gravity.

Results 40 grams of fluid were infused, which was delivered in 807 drops. The weight per drop of medical fluid delivered can be calculated:

$$40 \text{ grams}/807 \text{ drops}=0.04957 \text{ grams per drop.} \quad (1)$$

As discussed above, the specific gravity was set to be 0.9982 grams/ml. As a result, the volume per drop was calculated as follows:

$$0.04957 \text{ grams/drop}/0.9982 \text{ grams/mL}=0.04965 \text{ mL/drop.} \quad (2)$$

Example 2—Empirically Derived Medical Fluid Library Information

This example discusses empirical data loaded into the medical fluid library. As described above, the medical fluid library may include fluid properties, such as specific gravity and viscosity, of infused medical fluids, or infusates. In this example, the medical fluid library was loaded with empirically derived drop volumes, which can vary depending on the medical fluid being delivered, the flow rate, and the drip chamber specification. If the infuser does not have an operative weight sensor, the default drop size can be scaled according to values loaded into the medical fluid library. The drip chamber has a default number of drops expected per milliliter of fluid. For example, for a drip chamber with the specification of 60 drops per milliliter, the drop volume is expected to be 1/60=0.167 mL/drop. Actual drop volume delivered will vary depending on the medical fluid and the flow rate, as this experiment shows.

Methodology

In this experiment, three different drip chambers (60 drops per mL, 20 drops per mL, and 10 drops per mL) were used to deliver three medical fluids (20% Manitol, Propofol, saline). For each medical fluid, the flow rate was set to be 20 mL/hr, 300 mL/hr, and 1000 mL/hr. The number of drops and the total volume of fluid delivered were determined, which were then used to calculate the average drop volume.

Results

It was determined that, as the flow through a drop forming element increased, the volume of the drops created increased in a nonlinear manner. The volume of drops further depended on the medical fluid delivered. An empirically derived drop volume was calculated. These values are shown for representative infusates, flow rates, and drip chambers in Tables 1-3 below. Tables 1-3 show the values for 60 drops per mL, 20 drops per mL, and 10 drops per mL drip chambers, respectively.

TABLE 1

| Infusate | Drop volume at 20 mL/hr (mL) | Drop volume at 300 mL/hr (mL) | Drop volume at 1000 mL/hr (mL, |
|---|---|---|---|
| 20% Mannitol | 0.0171 | 0.0173 | 0.0188 |
| Propofol | 0.0169 | 0.0172 | 0.0178 |
| Normal saline | 0.0169 | 0.0175 | 0.0183 |

TABLE 2

| Infusate | Drop volume at 20 mL/hr (mL) | Drop volume at 300 mL/hr (mL) | Drop volume at 1000 mL/hr (mL) |
|---|---|---|---|
| 20% Mannitol | 0.050 | 0.055 | 0.059 |
| Propofol | 0.052 | 0.056 | 0.059 |
| Normal saline | 0.050 | 0.053 | 0.057 |

TABLE 3

| Infusate | Drop volume at 20 mL/hr (mL) | Drop volume at 300 mL/hr (mL) | Drop volume at 1000 mL/hr (mL) |
|---|---|---|---|
| 20% Mannitol | 0.095 | 0.105 | 0.114 |
| Propofol | 0.101 | 0.108 | 0.117 |
| Normal saline | 0.098 | 0.108 | 0.115 |

The above values can be stored in the medical fluid library in the form of, for example, a lookup table. For a specific medical fluid and a flow rate, the default drop volume determined by the drip chamber can be scaled up based on the empirically derived values for drop volume.

Example 3—Real-Time Computation of Flow Rate

During real-time monitoring of the flow rate, as described earlier, the central processor may be programmed to respond to specific drop events. In this experiment, the flow rate was calculated in real time based on the methodologies outlined in this disclosure.

Methodology

For each drop detected, save the very first of each run, a control event was generated and delivered to the central processor to implement the flow control algorithm. For each event, the time in milliseconds that elapsed since the previous drop was detected was recorded. The first drop event was withheld, as there was no prior drop event from which to compute an interval.

The control algorithm also included an algorithm to determine if the drop detector failed to detect a drop. The control algorithm inspected the drop interval and compared it to the previously processed drop events. If the new interval was within 10 percent of twice the previous interval, the algorithm interpreted this to be the result of the drop detection mechanism failing to detect a drop. This event was not used to compute a new flow and no adjustment to the control mechanism will be made, but an additional drop will be added to the drop count total. This situation is called a missing drop event. The control algorithm further included an interpretation of multiple consecutive missing drop events as a change in drop interval.

Results

The drop volume and drop interval were taken together to compute an instantaneous flow rate in milliliters per hour, as shown below:

$$0.04965 \text{ mL}/747 \text{ ms} \times 3600000 \text{ ms/hr} = 239.3 \text{ mL/hr} \quad (1)$$

The infusion apparatus steadily delivered drops at the rate of approximately 1 per second. A drop event is registered with an interval of 1.994 seconds. The range of values for the time interval (within 10% of 1 second) corresponding to a missing drop event is calculated as follows:

$$1 \text{ second} \times 2 \times 0.90 = 1.8 \text{ seconds and} \quad (2)$$

$$1 \text{ second} \times 2 \times 1.10 = 2.20 \text{ seconds}. \quad (3)$$

The expected drop interval was about 1 second, yet this interval was within the range of values corresponding to 10 percent of twice that value. Therefore, the algorithm concluded that another drop must have fallen about one second ago.

In the event that another drop of fluid fell within the same range, the interval would be processed as a single drop event and the new expected drop interval would be the current interval, e.g., approximately 2 seconds.

Other Embodiments

It is to be understood that while the inventions have been described in conjunction with the detailed description, the foregoing description and Examples are intended to illustrate and not limit the scope of the inventions, which are defined by the scope of the appended claims. Other aspects, advantages, and modifications are within the scope of the following claims.

What is claimed is:

1. An infusion apparatus that dispenses fluid from a fluid container into an outlet channel, the infusion apparatus comprising:
   a housing;
   a load connector attached to the housing and configured to accept the fluid container to be attached to the housing in a weight-bearing configuration;
   a chamber configured to be disposed in a fluid path between the fluid container and the outlet channel, wherein the chamber is configured to enable formation of drops as the fluid traverses the chamber;
   a weight sensor coupled to the load connector, wherein the weight sensor is configured to generate a weight signal based on a measured weight of the fluid container attached to the housing in the weight-bearing configuration;
   an optical sensor configured to generate drop signals based on detecting the drops of the fluid traversing the chamber;
   a flow control mechanism disposed in the fluid path between the fluid container and the outlet channel, wherein the flow control mechanism comprises a clamp member to engage the outlet channel to control a flow rate of the fluid in the outlet channel;
   one or more processing devices configured to execute machine-readable instructions to perform operations comprising:
   accessing a representation of a medical fluid library that includes information on fluid parameters for a plurality of medical fluids;
   computing a weighted average of estimates of the flow rate of the fluid based on the drop signals, the weight signal, and the fluid parameters of a selected medical fluid of the plurality of medical fluids; and
   transmitting a control signal to the flow control mechanism to adjust the flow rate of the fluid based on the weighted average of the estimates of the flow rate.

2. The infusion apparatus of claim 1, wherein the operations comprise computing at least one of the estimates by computing an expected drop sized based on the fluid parameters of the selected medical fluid.

3. The infusion apparatus of claim 1, wherein the operations comprise computing at least one of the estimates based on a pump speed of a volumetric pump of the infusion apparatus.

4. The infusion apparatus of claim 1, wherein the fluid parameters of the selected medical fluid comprise at least one of a specific gravity, a viscosity, or an opacity of the selected medical fluid.

5. The infusion apparatus of claim 1, wherein the housing comprises a receptacle for accepting an external cartridge that includes the chamber.

6. The infusion apparatus of claim 1, wherein the operations further comprise, before computing the weighted average of the estimates, receiving from a user interface a selection indicative of the selected medical fluid.

7. The infusion apparatus of claim 1, wherein the flow control mechanism comprises an electronically controllable clamp comprising the clamp member.

8. The infusion apparatus of claim 1, wherein the outlet channel comprises a tubing and the flow control mechanism operates on the tubing to control the flow rate of the fluid.

9. The infusion apparatus of claim 1, wherein the flow control mechanism comprises a volumetric pump configured to provide a substantially fixed volume of fluid per pumping cycle.

10. The infusion apparatus of claim 9, wherein the flow control mechanism is further configured to control the flow rate based on a pump speed of the volumetric pump.

11. An infusion apparatus for dispensing a fluid to an outlet channel, the infusion apparatus comprising:
a weight sensor module configured to generate a weight signal based on measuring a weight of a fluid container dispensing the fluid;
a flow sensor module configured to generate drop signals based on detecting drops of fluid formed in and traversing a fluid path connecting the fluid container and the outlet channel;
a flow control mechanism disposed in the fluid path between the fluid container and the outlet channel, wherein the flow control mechanism comprises a clamp member to engage the outlet channel to control a flow rate of the fluid in the outlet channel;
one or more processing devices configured to execute machine-readable instructions to perform operations comprising:
accessing a representation of a medical fluid library that includes information on fluid parameters for a plurality of medical fluids;
computing a weighted average of estimates of the flow rate of the fluid based on the drop signals, the weight signal, and the fluid parameters of a selected medical fluid of the plurality of medical fluids; and
transmitting a control signal to the flow control mechanism to adjust the flow rate of the fluid based on the weighted average of the estimates of the flow rate.

12. The infusion apparatus of claim 11, wherein the operations comprise computing at least one of the estimates by computing an expected drop sized based on the fluid parameters of the selected medical fluid.

13. The infusion apparatus of claim 11, wherein the operations comprise computing at least one of the estimates based on a pump speed of a volumetric pump of the infusion apparatus.

14. The infusion apparatus of claim 11, wherein the fluid parameters of the selected medical fluid comprises at least one of a specific gravity, a viscosity, and an opacity of the selected medical fluid.

15. An infusion apparatus that dispenses fluid from a fluid container into an outlet channel, the infusion apparatus comprising:
a housing;
a load connector attached to the housing and configured to accept the fluid container to be attached to the housing in a weight-bearing configuration;
a chamber configured to be disposed in a fluid path between the fluid container and the outlet channel, wherein the chamber is configured to enable formation of drops as the fluid traverses the chamber;
a weight sensor coupled to the load connector, wherein the weight sensor is configured to generate a weight signal based on a measured weight of the fluid container attached to the housing in the weight-bearing configuration;
an optical sensor configured to generate drop signals based on detecting the drops of the fluid traversing the chamber;
a flow control mechanism disposed in the fluid path between the fluid container and the outlet channel, wherein the flow control mechanism comprises a clamp member to engage the outlet channel to control a flow rate of the fluid in the outlet channel;
one or more processing devices configured to execute machine-readable instructions to perform operations comprising:
accessing a representation of a medical fluid library that includes information on fluid parameters for a plurality of medical fluids;
computing a first estimate of the flow rate of the fluid in a period of time based on comparing the drop signals in the period of time with the drop signals in a previous period of time;
computing a second estimate of the flow rate of the fluid based on the first estimate, the weight signal, and the fluid parameters of a selected medical fluid of the plurality of medical fluids; and
transmitting a control signal to the flow control mechanism to adjust the flow rate of the fluid responsive to determining a difference between a desired flow rate and the second estimate.

* * * * *